US009192566B2

(12) United States Patent
Soltani et al.

(10) Patent No.: US 9,192,566 B2
(45) Date of Patent: Nov. 24, 2015

(54) TREATMENT OF VASCULAR OCCLUSIONS USING ULTRASONIC ENERGY AND MICROBUBBLES

(71) Applicant: Ekos Corporation, Bothell, WA (US)

(72) Inventors: Azita Soltani, Snohomish, WA (US); Douglas R. Hansmann, Bainbridge Island, WA (US)

(73) Assignee: EKOS CORPORATION, Bothell, WA (US)

( * ) Notice: Subject to any disclaimer, the term of this patent is extended or adjusted under 35 U.S.C. 154(b) by 0 days.

(21) Appl. No.: 14/255,834

(22) Filed: Apr. 17, 2014

(65) Prior Publication Data
US 2014/0316329 A1 Oct. 23, 2014

Related U.S. Application Data

(63) Continuation of application No. 13/029,962, filed on Feb. 17, 2011, now Pat. No. 8,740,835.

(60) Provisional application No. 61/305,477, filed on Feb. 17, 2010.

(51) Int. Cl.
A61K 9/00 (2006.01)
A61N 7/02 (2006.01)
(Continued)

(52) U.S. Cl.
CPC ........... *A61K 9/0009* (2013.01); *A61B 17/2202* (2013.01); *A61N 7/022* (2013.01); *A61B 2017/22021* (2013.01); *A61B 2018/00023* (2013.01); *A61B 2018/00648* (2013.01); *A61B 2018/00797* (2013.01); *A61N 2007/0039* (2013.01)

(58) Field of Classification Search
CPC ............. A61K 9/0009; A61B 17/2202; A61B 2018/00797; A61B 2018/00648; A61B 2018/00023; A61B 2017/22021; A61N 7/022; A61N 2007/0039
USPC .......................................................... 604/22
See application file for complete search history.

(56) References Cited

U.S. PATENT DOCUMENTS 3,430,625 A 3/1969 McLeod, Jr.
3,433,226 A 3/1969 Boyd
(Continued)

FOREIGN PATENT DOCUMENTS

EP 0 744 189 11/1996
EP 1 090 658 4/2001
(Continued)

OTHER PUBLICATIONS

Butler PhD, Bruce D., "Production of Microbubbles for Use as Echo Contrast Agents", Journal of Clinical Ultrasound, Jun. 1986, vol. 14, pp. 408-412.
(Continued)

Primary Examiner — Manuel Mendez
(74) Attorney, Agent, or Firm — Knobbe, Martens, Olson & Bear, LLP

(57) ABSTRACT

In one embodiment of the present invention, a method of treating a vascular occlusion located at a treatment site within a patient's vasculature comprises positioning an ultrasound catheter at the treatment site. The method further comprises delivering a microbubble-therapeutic compound from the ultrasound catheter to the vascular occlusion during a first treatment phase.

10 Claims, 19 Drawing Sheets

(51) Int. Cl.
*A61B 17/22* (2006.01)
*A61B 18/00* (2006.01)
*A61N 7/00* (2006.01)

(56) References Cited

U.S. PATENT DOCUMENTS

| | | |
|---|---|---|
| 3,565,062 A | 2/1971 | Kuris |
| 3,827,115 A | 8/1974 | Bom |
| 3,941,122 A | 3/1976 | Jones |
| 4,192,294 A | 3/1980 | Vasilevsky et al. |
| 4,309,989 A | 1/1982 | Fahim |
| 4,319,580 A | 3/1982 | Colley et al. |
| 4,354,502 A | 10/1982 | Colley et al. |
| 4,750,902 A | 6/1988 | Wuchinich |
| 4,772,594 A | 9/1988 | Hashimoto et al. |
| 4,870,953 A | 10/1989 | DonMicheal et al. |
| 4,936,281 A | 6/1990 | Stasz |
| 4,948,587 A | 8/1990 | Kost et al. |
| 4,953,565 A | 9/1990 | Tachibana et al. |
| 4,971,991 A | 11/1990 | Umemura et al. |
| 5,088,499 A | 2/1992 | Unger |
| 5,158,071 A | 10/1992 | Umemura et al. |
| 5,163,421 A | 11/1992 | Bernstein et al. |
| 5,163,436 A | 11/1992 | Saitoh et al. |
| 5,197,946 A | 3/1993 | Tachibana |
| 5,267,954 A | 12/1993 | Nita |
| 5,269,291 A | 12/1993 | Carter |
| 5,279,546 A | 1/1994 | Mische et al. |
| 5,307,816 A | 5/1994 | Hashimoto |
| 5,312,328 A | 5/1994 | Nita et al. |
| 5,315,998 A | 5/1994 | Tachibana et al. |
| 5,318,014 A | 6/1994 | Carter |
| 5,342,292 A | 8/1994 | Nita et al. |
| 5,344,395 A | 9/1994 | Whalen et al. |
| 5,362,309 A | 11/1994 | Carter |
| 5,368,557 A | 11/1994 | Nita |
| 5,368,558 A | 11/1994 | Nita |
| 5,380,273 A | 1/1995 | Dubrul et al. |
| 5,401,237 A | 3/1995 | Tachibana et al. |
| 5,431,663 A | 7/1995 | Carter |
| 5,440,914 A | 8/1995 | Tachibana et al. |
| 5,447,509 A | 9/1995 | Mills et al. |
| 5,456,259 A | 10/1995 | Barlow et al. |
| 5,474,531 A | 12/1995 | Carter |
| 5,509,896 A | 4/1996 | Carter |
| 5,542,917 A | 8/1996 | Nita et al. |
| 5,542,935 A | 8/1996 | Unger et al. |
| 5,558,092 A | 9/1996 | Unger et al. |
| 5,582,586 A | 12/1996 | Tachibana et al. |
| 5,620,409 A | 4/1997 | Gans et al. |
| 5,620,479 A | 4/1997 | Diederich |
| 5,624,382 A | 4/1997 | Oppelt |
| 5,628,728 A | 5/1997 | Tachibana et al. |
| 5,630,837 A | 5/1997 | Crowley |
| 5,648,098 A | 7/1997 | Porter |
| 5,660,909 A | 8/1997 | Tachibana et al. |
| 5,681,296 A | 10/1997 | Ishida |
| 5,695,460 A | 12/1997 | Siegel et al. |
| 5,720,710 A | 2/1998 | Tachibana et al. |
| 5,724,976 A | 3/1998 | Hirama et al. |
| 5,725,494 A | 3/1998 | Brisken |
| 5,728,062 A | 3/1998 | Brisken |
| 5,735,811 A | 4/1998 | Brisken |
| 5,752,930 A | 5/1998 | Baudino et al. |
| 5,823,962 A | 10/1998 | Lerch et al. |
| 5,827,203 A | 10/1998 | Nita |
| 5,834,880 A | 11/1998 | Lewandowski et al. |
| 5,836,896 A | 11/1998 | Rosenschein |
| 5,836,940 A | 11/1998 | Gregory |
| 5,840,031 A | 11/1998 | Crowley |
| 5,846,218 A | 12/1998 | Brisken et al. |
| 5,846,517 A | 12/1998 | Unger |
| 5,876,345 A | 3/1999 | Eaton et al. |
| 5,916,192 A | 6/1999 | Nita et al. |
| 5,925,016 A | 7/1999 | Chornenky et al. |
| 5,928,186 A | 7/1999 | Homsma et al. |
| 5,931,805 A | 8/1999 | Brisken |
| 5,957,851 A | 9/1999 | Hossack |
| 5,957,882 A | 9/1999 | Nita et al. |
| 5,971,949 A | 10/1999 | Levin et al. |
| 5,976,120 A | 11/1999 | Chow et al. |
| 5,997,497 A | 12/1999 | Nita et al. |
| 6,001,069 A | 12/1999 | Tachibana et al. |
| 6,007,514 A | 12/1999 | Nita |
| 6,063,069 A | 5/2000 | Cragg et al. |
| 6,066,123 A | 5/2000 | Bednarski et al. |
| 6,088,613 A | 7/2000 | Unger |
| 6,089,573 A | 7/2000 | Udagawa |
| 6,096,000 A | 8/2000 | Tachibana et al. |
| 6,113,558 A | 9/2000 | Rosenschein et al. |
| 6,113,570 A | 9/2000 | Siegel et al. |
| 6,117,101 A | 9/2000 | Diederich et al. |
| RE36,939 E | 10/2000 | Tachibana et al. |
| 6,135,976 A | 10/2000 | Tachibana et al. |
| 6,149,596 A | 11/2000 | Bancroft |
| 6,176,842 B1 | 1/2001 | Tachibana et al. |
| 6,206,831 B1 | 3/2001 | Suorsa et al. |
| 6,210,356 B1 | 4/2001 | Anderson et al. |
| 6,210,393 B1 | 4/2001 | Brisken |
| 6,221,038 B1 | 4/2001 | Brisken |
| 6,228,046 B1 | 5/2001 | Brisken |
| 6,235,024 B1 | 5/2001 | Tu |
| 6,238,347 B1 | 5/2001 | Nix et al. |
| 6,270,460 B1 | 8/2001 | McCartan et al. |
| 6,277,077 B1 | 8/2001 | Brisken et al. |
| 6,287,271 B1 | 9/2001 | Dubrul et al. |
| 6,296,619 B1 | 10/2001 | Brisken et al. |
| 6,312,402 B1 | 11/2001 | Hansmann |
| 6,361,554 B1 | 3/2002 | Brisken |
| 6,391,042 B1 | 5/2002 | Cimino |
| 6,398,772 B1 | 6/2002 | Bond et al. |
| 6,416,740 B1 | 7/2002 | Unger |
| 6,464,680 B1 | 10/2002 | Brisken et al. |
| 6,471,683 B2 | 10/2002 | Drasier et al. |
| 6,478,765 B2 | 11/2002 | Siegel et al. |
| 6,506,584 B1 | 1/2003 | Chandler et al. |
| 6,524,251 B2 | 2/2003 | Rabiner et al. |
| 6,524,271 B2 | 2/2003 | Brisken et al. |
| 6,524,300 B2 | 2/2003 | Meglin |
| 6,551,337 B1 | 4/2003 | Rabiner et al. |
| 6,558,366 B1 | 5/2003 | Drasler et al. |
| 6,562,021 B1 | 5/2003 | Derbin et al. |
| 6,565,552 B1 | 5/2003 | Barbut |
| 6,575,956 B1 | 6/2003 | Brisken et al. |
| 6,579,277 B1 | 6/2003 | Rabiner et al. |
| 6,582,392 B1 | 6/2003 | Bennett et al. |
| 6,585,678 B1 | 7/2003 | Tachibana et al. |
| 6,605,084 B2 | 8/2003 | Acker et al. |
| 6,635,017 B1 | 10/2003 | Moehring et al. |
| 6,635,046 B1 | 10/2003 | Barbut |
| 6,645,150 B2 | 11/2003 | Angelsen et al. |
| 6,647,755 B2 | 11/2003 | Rabiner et al. |
| 6,652,547 B2 | 11/2003 | Rabiner et al. |
| 6,660,013 B2 | 12/2003 | Rabiner |
| 6,663,613 B1 | 12/2003 | Evans et al. |
| 6,676,626 B1 | 1/2004 | Bennett et al. |
| 6,682,502 B2 | 1/2004 | Bond et al. |
| 6,689,086 B1 | 2/2004 | Nita et al. |
| 6,695,781 B2 | 2/2004 | Rabiner et al. |
| 6,695,782 B2 | 2/2004 | Ranucci et al. |
| 6,695,785 B2 | 2/2004 | Brisken et al. |
| 6,723,063 B1 | 4/2004 | Zhang et al. |
| 6,726,698 B2 | 4/2004 | Cimino |
| 6,730,048 B1 | 5/2004 | Hare et al. |
| 6,733,451 B2 | 5/2004 | Rabiner et al. |
| 6,740,040 B1 | 5/2004 | Mandrusov et al. |
| 6,767,345 B2 | 7/2004 | St. Germain et al. |
| 6,824,575 B1 | 11/2004 | Otomo et al. |
| 6,830,577 B2 | 12/2004 | Nash et al. |
| 6,849,062 B2 | 2/2005 | Kantor |
| 6,855,123 B2 | 2/2005 | Nita |
| 6,866,670 B2 | 3/2005 | Rabiner et al. |
| 6,896,659 B2 | 5/2005 | Conston et al. |
| 6,905,505 B2 | 6/2005 | Dodson, Jr. et al. |

(56) References Cited

U.S. PATENT DOCUMENTS

| | | |
|---|---|---|
| 6,921,371 B2 | 7/2005 | Wilson |
| 6,929,633 B2 | 8/2005 | Evans et al. |
| 6,942,620 B2 | 9/2005 | Nita et al. |
| 6,945,937 B2 | 9/2005 | Culp et al. |
| 6,958,040 B2 | 10/2005 | Oliver et al. |
| 6,979,293 B2 | 12/2005 | Hansmann et al. |
| 6,985,771 B2 | 1/2006 | Fischell et al. |
| 7,137,963 B2 | 11/2006 | Nita et al. |
| 7,141,044 B2 | 11/2006 | Gentsler |
| 7,166,098 B1 | 1/2007 | Steward et al. |
| 7,186,246 B2 | 3/2007 | Bennett et al. |
| 7,220,233 B2 | 5/2007 | Nita et al. |
| 7,220,239 B2 | 5/2007 | Wilson et al. |
| 7,309,334 B2 | 12/2007 | von Hoffmann |
| 7,335,180 B2 | 2/2008 | Nita et al. |
| 7,341,569 B2 | 3/2008 | Soltani et al. |
| 7,503,895 B2 | 3/2009 | Rabiner et al. |
| 7,540,852 B2 | 6/2009 | Nita et al. |
| 7,567,016 B2 | 7/2009 | Lu et al. |
| 7,604,608 B2 | 10/2009 | Nita et al. |
| 7,621,902 B2 | 11/2009 | Nita et al. |
| 7,648,478 B2 | 1/2010 | Soltani et al. |
| 7,758,509 B2 | 7/2010 | Angelsen et al. |
| 7,771,372 B2 | 8/2010 | Wilson |
| 7,789,830 B2 | 9/2010 | Fujita et al. |
| 7,828,754 B2 | 11/2010 | Abe et al. |
| 7,901,359 B2 | 3/2011 | Mandrusov et al. |
| 7,914,509 B2 | 3/2011 | Bennett et al. |
| 8,012,092 B2 | 9/2011 | Powers et al. |
| 8,062,566 B2 | 11/2011 | Nita et al. |
| 8,123,789 B2 | 2/2012 | Khanna |
| 8,152,753 B2 | 4/2012 | Nita et al. |
| 8,740,835 B2 | 6/2014 | Soltani et al. |
| 2002/0032394 A1 | 3/2002 | Brisken et al. |
| 2002/0045890 A1 | 4/2002 | Celliers et al. |
| 2002/0052620 A1 | 5/2002 | Barbut |
| 2002/0068869 A1 | 6/2002 | Brisken et al. |
| 2002/0077550 A1 | 6/2002 | Rabiner et al. |
| 2002/0082238 A1 | 6/2002 | Newman et al. |
| 2002/0123787 A1 | 9/2002 | Weiss |
| 2002/0133111 A1 | 9/2002 | Shadduck |
| 2002/0193708 A1 | 12/2002 | Thompson et al. |
| 2003/0036705 A1 | 2/2003 | Hare et al. |
| 2003/0040501 A1 | 2/2003 | Newman et al. |
| 2003/0050662 A1 | 3/2003 | Don Michael |
| 2003/0065263 A1 | 4/2003 | Hare et al. |
| 2003/0069525 A1 | 4/2003 | Brisken et al. |
| 2003/0163147 A1 | 8/2003 | Hare et al. |
| 2003/0191446 A1 | 10/2003 | Tachibana et al. |
| 2003/0236539 A1 | 12/2003 | Rabiner et al. |
| 2004/0001809 A1 | 1/2004 | Brisken et al. |
| 2004/0010290 A1 | 1/2004 | Schroeppel et al. |
| 2004/0019318 A1 | 1/2004 | Wilson et al. |
| 2004/0024393 A1 | 2/2004 | Nita et al. |
| 2004/0039311 A1 | 2/2004 | Nita et al. |
| 2004/0049148 A1 | 3/2004 | Rodriguez et al. |
| 2004/0054351 A1 | 3/2004 | Deniega et al. |
| 2004/0059313 A1 | 3/2004 | Anderson et al. |
| 2004/0068189 A1 | 4/2004 | Wilson et al. |
| 2004/0097996 A1 | 5/2004 | Hare et al. |
| 2004/0138570 A1 | 7/2004 | Nita et al. |
| 2004/0162571 A1 | 8/2004 | Rabiner et al. |
| 2004/0171981 A1 | 9/2004 | Buffen et al. |
| 2004/0220514 A1 | 11/2004 | Cafferata |
| 2004/0220544 A1 | 11/2004 | Heruth et al. |
| 2004/0236350 A1 | 11/2004 | Bolduc et al. |
| 2004/0255957 A1 | 12/2004 | Cafferata |
| 2004/0265393 A1 | 12/2004 | Unger et al. |
| 2005/0021063 A1 | 1/2005 | Hall et al. |
| 2005/0043629 A1 | 2/2005 | Rabiner et al. |
| 2005/0043753 A1 | 2/2005 | Rabiner et al. |
| 2005/0090818 A1 | 4/2005 | Pike, Jr. et al. |
| 2005/0096669 A1 | 5/2005 | Rabiner et al. |
| 2005/0113688 A1 | 5/2005 | Nita et al. |
| 2005/0119679 A1 | 6/2005 | Rabiner et al. |
| 2005/0124877 A1 | 6/2005 | Nita et al. |
| 2005/0137520 A1 | 6/2005 | Rule et al. |
| 2005/0187513 A1 | 8/2005 | Rabiner et al. |
| 2005/0187514 A1 | 8/2005 | Rabiner et al. |
| 2005/0197619 A1 | 9/2005 | Rule et al. |
| 2005/0209578 A1 | 9/2005 | Evans et al. |
| 2005/0215942 A1 | 9/2005 | Abrahamson et al. |
| 2005/0215946 A1 | 9/2005 | Hansmann et al. |
| 2005/0216044 A1 | 9/2005 | Hong |
| 2005/0256410 A1 | 11/2005 | Rabiner et al. |
| 2006/0069303 A1 | 3/2006 | Couvillon |
| 2006/0106308 A1 | 5/2006 | Hansmann et al. |
| 2006/0173387 A1 | 8/2006 | Hansmann et al. |
| 2006/0184070 A1 | 8/2006 | Hansmann et al. |
| 2007/0037119 A1 | 2/2007 | Pal et al. |
| 2007/0066978 A1 | 3/2007 | Schafer et al. |
| 2007/0207194 A1 | 9/2007 | Grayburn et al. |
| 2007/0225619 A1 | 9/2007 | Rabiner et al. |
| 2007/0239027 A1 | 10/2007 | Nita |
| 2007/0265560 A1 | 11/2007 | Soltani et al. |
| 2008/0045865 A1 | 2/2008 | Kislev |
| 2008/0065014 A1 | 3/2008 | McCrystle et al. |
| 2008/0154181 A1 | 6/2008 | Khanna |
| 2008/0167602 A1 | 7/2008 | Nita et al. |
| 2008/0171965 A1 | 7/2008 | Soltani et al. |
| 2008/0172067 A1 | 7/2008 | Nita et al. |
| 2008/0194954 A1 | 8/2008 | Matsunaga et al. |
| 2008/0221506 A1 | 9/2008 | Rodriguez et al. |
| 2008/0262350 A1 | 10/2008 | Unger |
| 2008/0274097 A1 | 11/2008 | Tachibana |
| 2008/0306499 A1 | 12/2008 | Katoh et al. |
| 2008/0319355 A1 | 12/2008 | Nita |
| 2008/0319376 A1 | 12/2008 | Wilcox et al. |
| 2009/0018472 A1 | 1/2009 | Soltani et al. |
| 2009/0112150 A1 | 4/2009 | Unger et al. |
| 2009/0216246 A1 | 8/2009 | Nita et al. |
| 2010/0010393 A1 | 1/2010 | Duffy et al. |
| 2010/0063413 A1 | 3/2010 | Volz |
| 2010/0063414 A1 | 3/2010 | Volz |
| 2010/0081934 A1 | 4/2010 | Hansmann et al. |
| 2010/0204582 A1 | 8/2010 | Lu |
| 2010/0210940 A1 | 8/2010 | Bradley et al. |
| 2010/0222715 A1 | 9/2010 | Nita |
| 2010/0256616 A1 | 10/2010 | Katoh et al. |
| 2010/0262215 A1 | 10/2010 | Gertner |
| 2010/0292685 A1 | 11/2010 | Katoh et al. |
| 2011/0160621 A1 | 6/2011 | Nita |
| 2011/0201974 A1* | 8/2011 | Soltani et al. ............... 601/2 |
| 2011/0264031 A1 | 10/2011 | Soltani et al. |
| 2011/0288449 A1 | 11/2011 | Schenkengel |
| 2011/0300078 A1* | 12/2011 | Borden et al. ............ 424/9.52 |
| 2011/0313328 A1 | 12/2011 | Nita |
| 2011/0319927 A1 | 12/2011 | Nita |
| 2012/0016272 A1 | 1/2012 | Nita et al. |
| 2012/0041307 A1 | 2/2012 | Patel et al. |
| 2012/0059285 A1 | 3/2012 | Soltani et al. |
| 2012/0078140 A1 | 3/2012 | Nita |
| 2012/0123273 A1 | 5/2012 | Okuno et al. |
| 2012/0179073 A1 | 7/2012 | Nita |
| 2012/0197277 A1 | 8/2012 | Stinis |
| 2013/0204166 A1* | 8/2013 | Villanueva et al. .......... 601/2 |
| 2013/0216593 A1* | 8/2013 | Borden et al. ............. 424/400 |
| 2013/0289398 A1* | 10/2013 | Borden et al. ............ 600/431 |
| 2013/0331738 A1* | 12/2013 | Borrelli ....................... 601/2 |
| 2014/0236005 A1* | 8/2014 | Chen et al. ................ 600/433 |

FOREIGN PATENT DOCUMENTS

| | | |
|---|---|---|
| JP | 52115591 | 9/1977 |
| WO | WO 96/27341 | 9/1996 |
| WO | WO 96/29935 | 10/1996 |
| WO | WO 96/36286 | 11/1996 |
| WO | WO 98/18391 | 5/1998 |
| WO | WO 98/48711 | 11/1998 |
| WO | WO 99/33500 | 7/1999 |
| WO | WO 99/39647 | 8/1999 |
| WO | WO 00/38580 | 7/2000 |
| WO | WO 01/95788 | 12/2001 |
| WO | WO 02/13678 | 2/2002 |

(56) References Cited

FOREIGN PATENT DOCUMENTS

| WO | WO 02/15803 | 2/2002 |
|---|---|---|
| WO | WO 02/15804 | 2/2002 |
| WO | WO 03/051208 | 6/2003 |
| WO | WO 2005/027756 | 3/2005 |
| WO | WO 2005/084552 | 9/2005 |
| WO | WO 2005/084553 | 9/2005 |
| WO | WO 2007/127176 | 11/2007 |

OTHER PUBLICATIONS

Bleeker et al., "On the Application of Ultrasonic Contrast Agents for Blood Flowmetry and Assessment of Cardiac Perfusion", Journal of Ultrasound in Medicine, Aug. 1990, vol. 9, No. 8, pp. 461-471.

Feinstein et al., "Two-dimensional Contrast Echocardiography. I. In Vitro Development and Quantitative Analysis of Echo Contrast Agents", Journal of the American College of Cardiology, Jan. 1984, vol. 3, No. 1, pp. 14-20.

Holland et al., "Thresholds for Transient Cavitation Produced by Pulsed Ultrasound in a Controlled Nuclei Environment", The Journal of the Acoustical Society of America, Nov. 1990, vol. 88, No. 5, pp. 2059-2069.

Keller et al., "Automated Production and Analysis of Echo Contrast Agents", Journal of Ultrasound in Medicine, Sep. 1986, vol. 5, pp. 493-498.

Kim, Timothy F., "Microbubbles Show Promise for Enhancing Ultrasound Signal, Image, Other Applications", The Journal of the American Medical Association, Mar. 1989, vol. 281, No. 11, p. 1542.

Lang et al., "Contrast Ultrasonography of the Kidney: a New Method for Evaluation of Renal Perfusion in Vivo", Circulation, 1987, vol. 75, No. 1, pp. 229-234.

Leong et al., "Polyanhydrides for Controlled Release of Bioactive Agents", Biomaterials, Sep. 1986, vol. 7, pp. 364-371.

Meltzer et al., "The Source of Ultrasound Contrast Effect", Journal of Clinical Ultrasound, Apr. 1980, vol. 8, No. 2, pp. 121-127.

Vandenburg et al., "Myocardial Risk Area and Peak Gray Level Measurement by Contrast Echocardiography: Effect of Microbubble Size and Concentration, Injection Rate, and Coronary Vasodilation," American Heart Journal, Apr. 1988, vol. 115, No. 4, pp. 733-739.

Wheatly et al., "Contrast Agents for Diagnostic Ultrasound: Development and Evaluation of Polymer-Coated Microbubbles," Biomaterials, Nov. 1990, vol. 11, No. 19, pp. 713-717.

\* cited by examiner

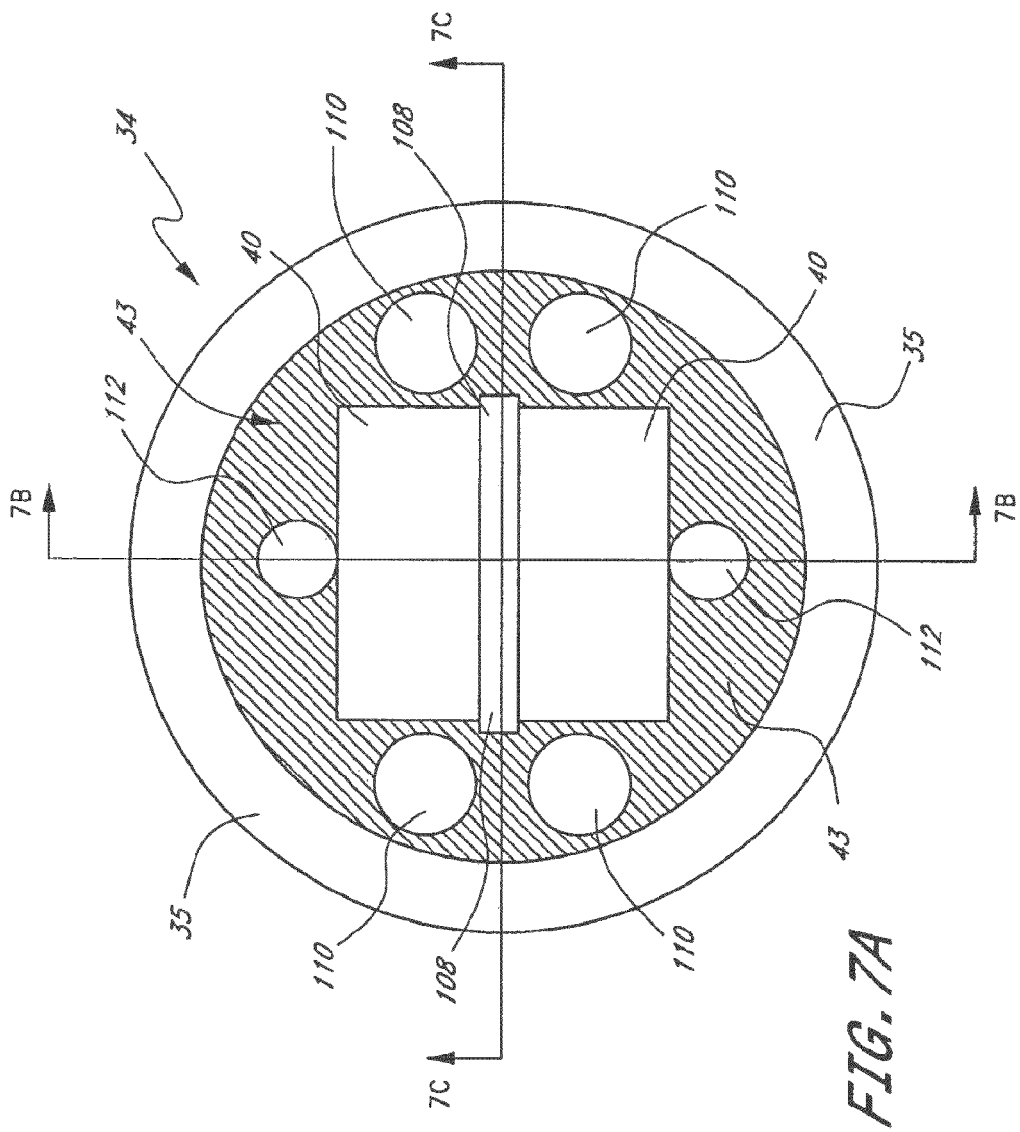

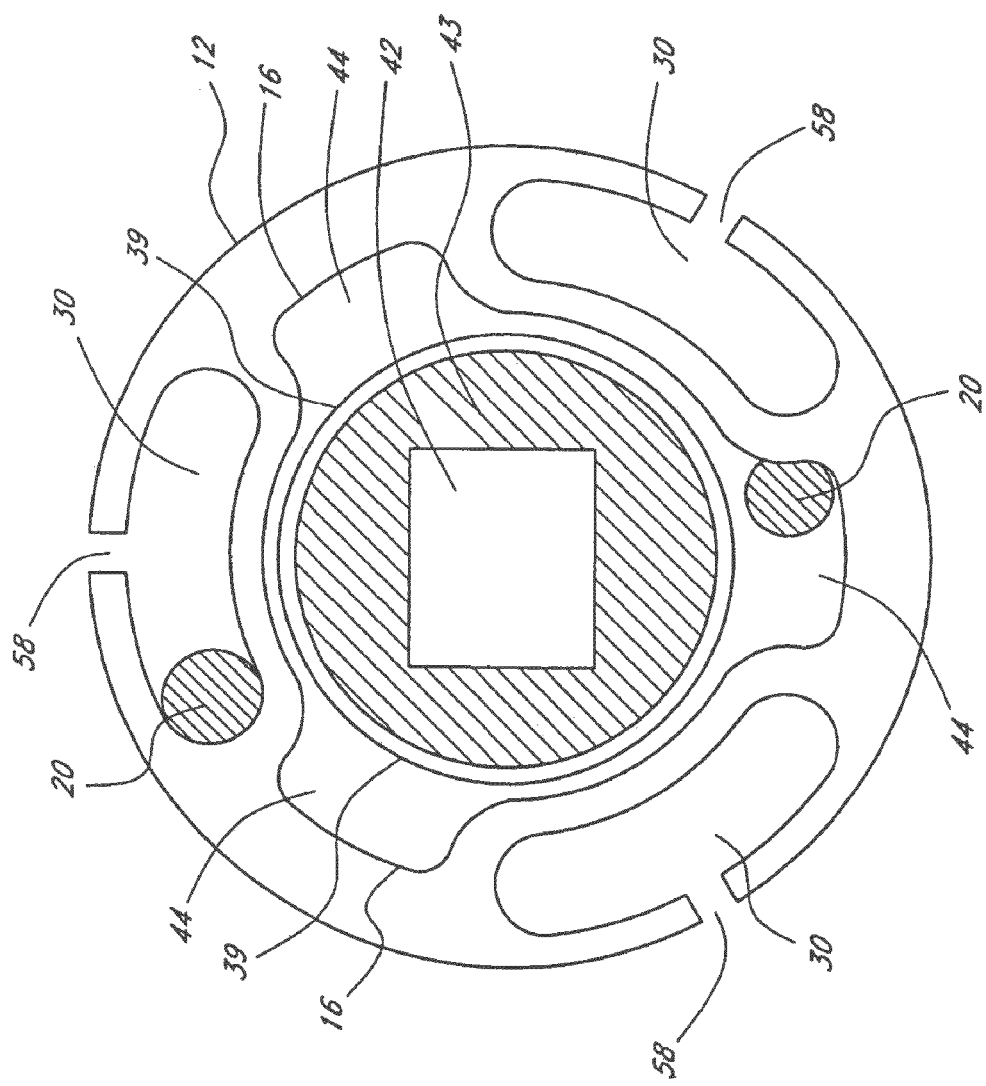

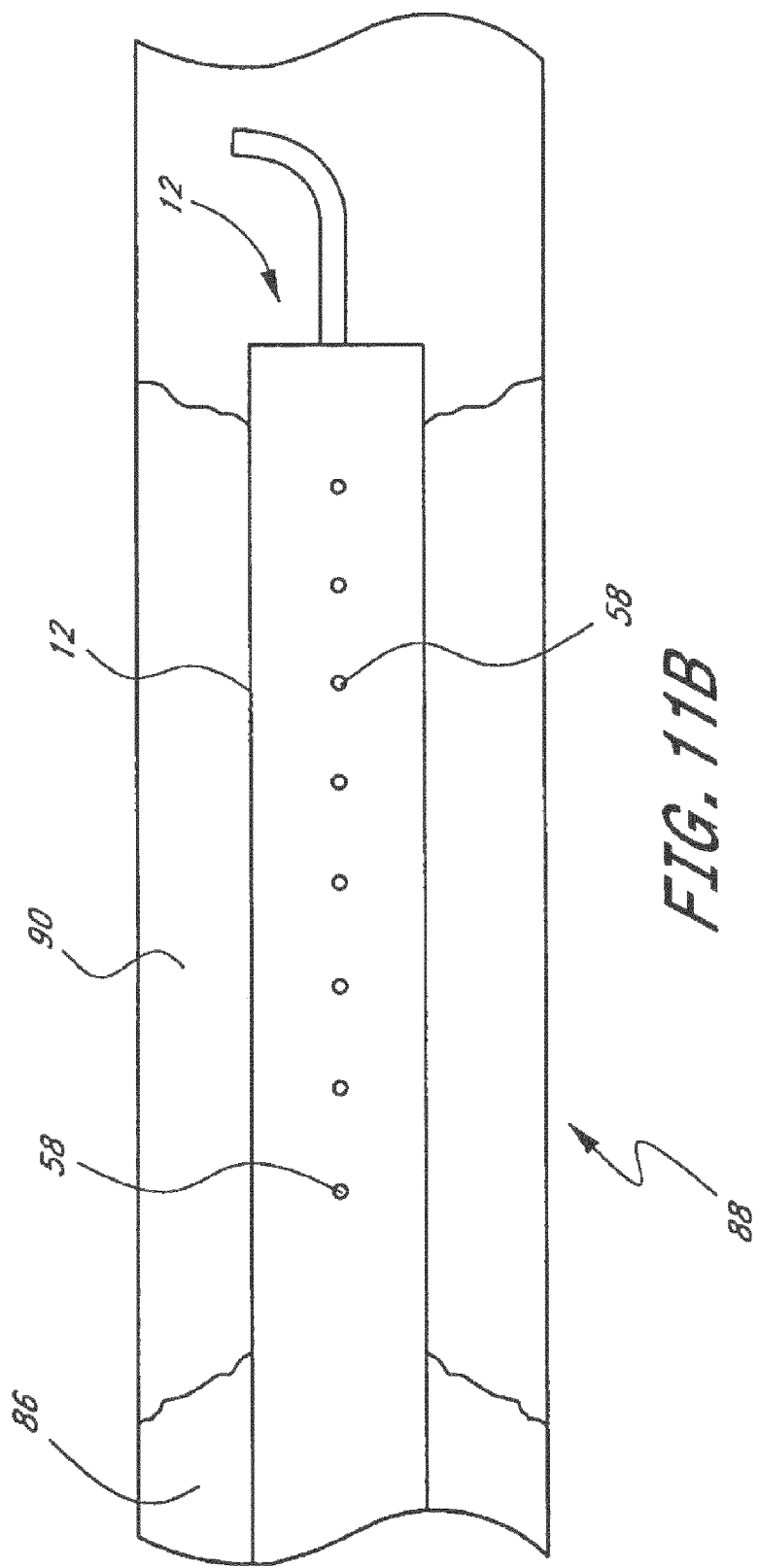

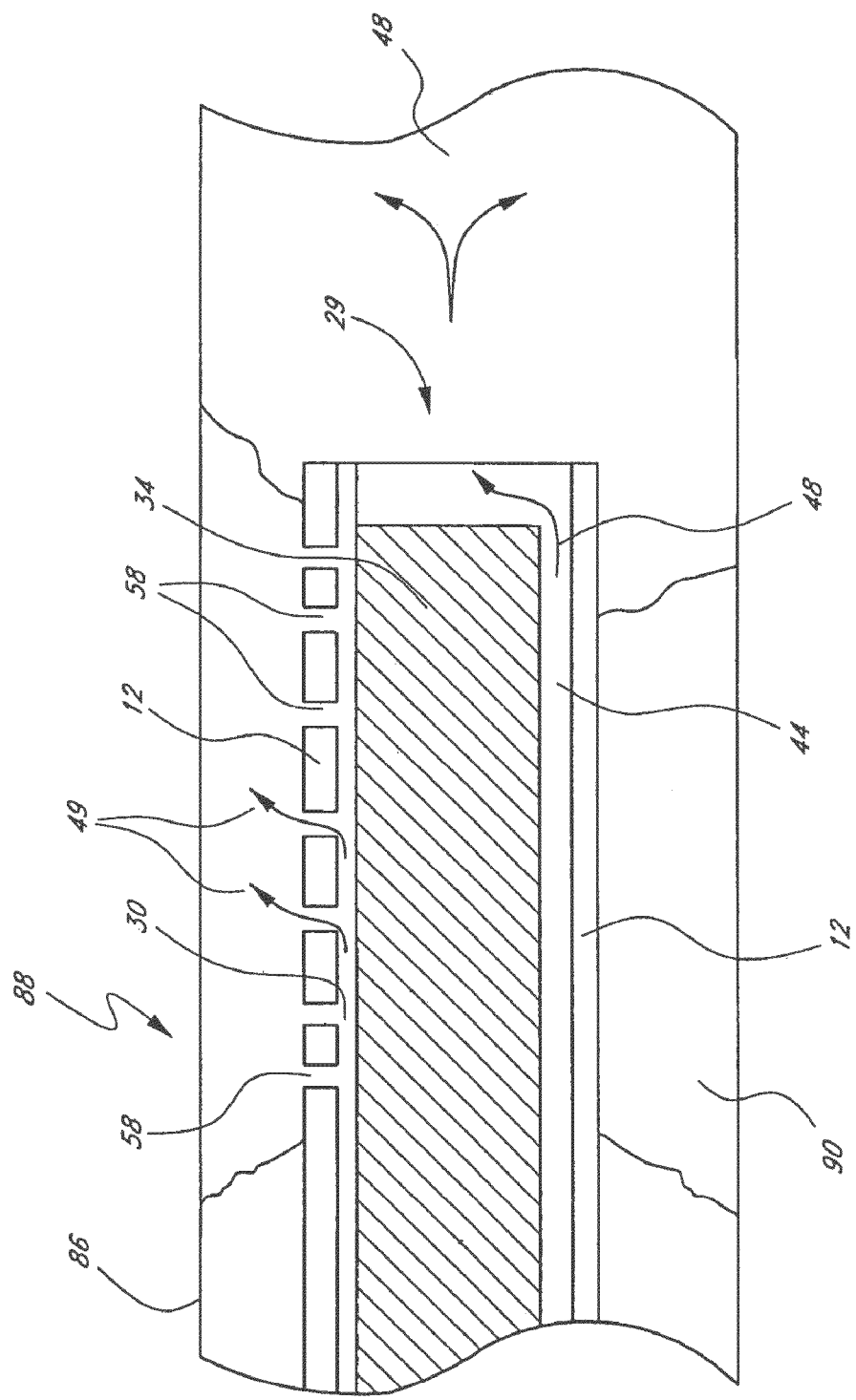

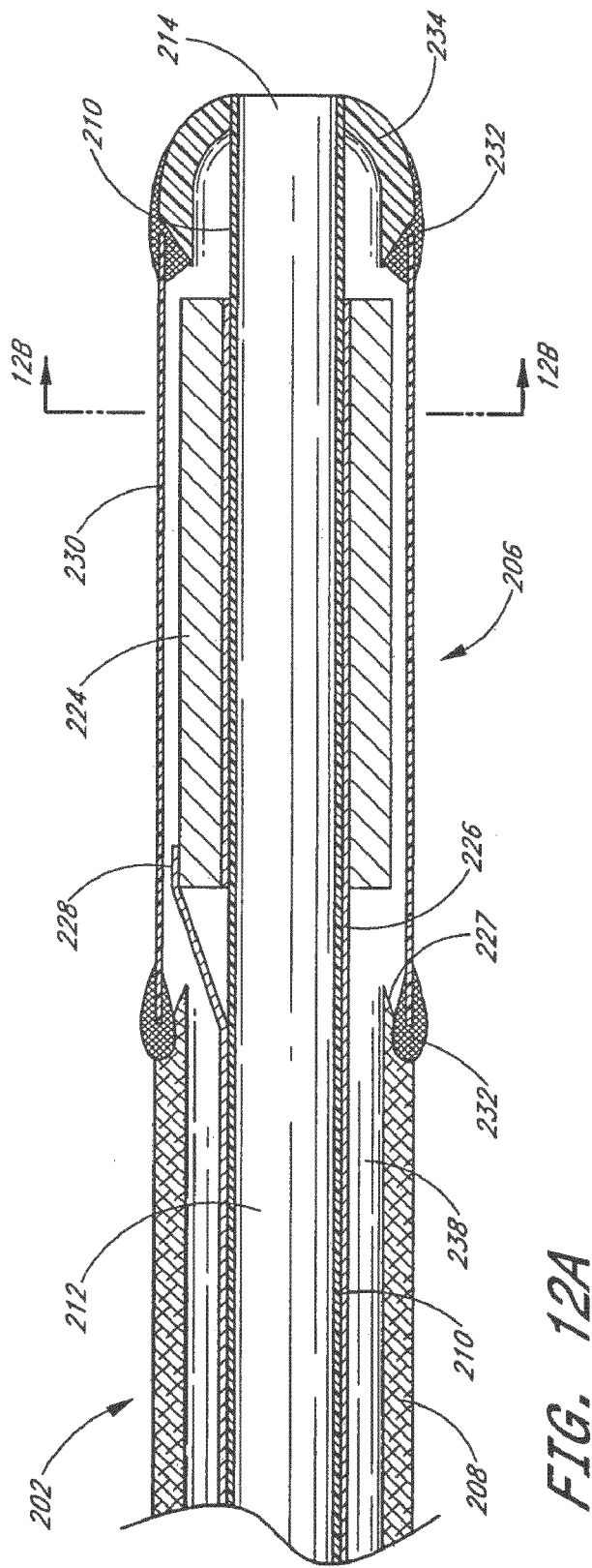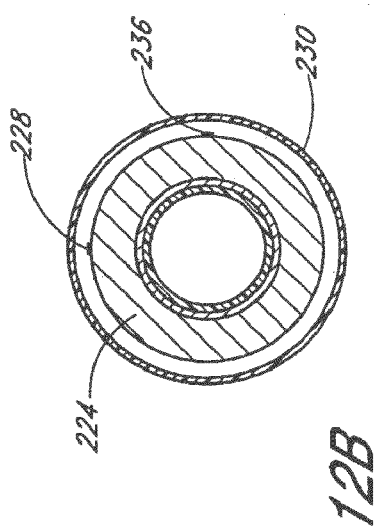
FIG. 12A
FIG. 12B

TREATMENT OF VASCULAR OCCLUSIONS USING ULTRASONIC ENERGY AND MICROBUBBLES

CROSS-REFERENCE TO RELATED APPLICATIONS

This is a continuation of U.S. patent application Ser. No. 13/029,962, filed Feb. 17, 2011, now U.S. Pat. No. 8,740,835, which claims the priority benefit of U.S. Provisional Application No. 61/305,477, filed Feb. 17, 2010, the entire contents of these applications are hereby incorporated by reference herein.

STATEMENT REGARDING FEDERALLY SPONSORED R&D

The invention was made with government support under Grant No. R21 NS053418-01A1 awarded by the National Institutes of Health. The government has certain rights to the invention.

BACKGROUND

1. Field of the Invention

The present invention relates generally to treatment of vascular occlusions, and more specifically to treatment of vascular occlusions with ultrasonic energy and a therapeutic compound combined with microbubbles.

2. Background of the Invention

Several medical applications use ultrasonic energy. For example, U.S. Pat. Nos. 4,821,740, 4,953,565 and 5,007,438 disclose the use of ultrasonic energy to enhance the effect of various therapeutic compounds. An ultrasonic catheter can be used to deliver ultrasonic energy and a therapeutic compound to a treatment site within a patient's body. Such an ultrasonic catheter typically includes an ultrasound assembly configured to generate ultrasonic energy and a fluid delivery lumen for delivering the therapeutic compound to the treatment site.

As taught in U.S. Pat. No. 6,001,069, ultrasonic catheters can be used to treat human blood vessels that have become partially or completely occluded by plaque, thrombi, emboli or other substances that reduce the blood carrying capacity of the vessel. To remove or reduce the occlusion, the ultrasonic catheter is used to deliver solutions containing therapeutic compounds directly to the occlusion site. Ultrasonic energy generated by the ultrasound assembly enhances the effect of the therapeutic compounds. Such a device can be used in the treatment of diseases such as peripheral arterial occlusion, deep vein thrombosis or acute ischemic stroke. In such applications, the ultrasonic energy enhances treatment of the occlusion with therapeutic compounds such as urokinase, tissue plasminogen activator ("tPA"), recombinant tissue plasminogen activator ("rtPA") and the like. Further information on enhancing the effect of a therapeutic compound using ultrasonic energy is provided in U.S. Pat. Nos. 5,318,014, 5,362,309, 5,474,531, 5,628,728, 6,001,069, 6,210,356 and 7,341,569.

SUMMARY OF THE INVENTION

Certain therapeutic compounds contain a plurality of microbubbles having, for example, a gas formed therein or can be combined with microbubbles prior to the treatment initiation. The efficacy of a therapeutic compound can be enhanced by the presence of the microbubbles contained therein in presence of ultrasound energy. The microbubbles act as a nucleus for cavitation, which can accelerate the dissolution and removal of a vascular occlusion. In relatively low acoustic rarefaction pressure amplitude a bubble could experience prolonged linear or nonlinear oscillation about its equilibrium radius (stable cavitation) or could experience a violent collapse followed by an unstable expansion of the bubble radius (inertial cavitation). It is unlikely that stable cavitation causes mechanical disruption of the clot. The violent collapse of an inertial bubble, however, releases a significant amount of energy in the form of an acoustic shock wave that could potentiate clot fragmentation. Both stable and inertial cavitation with their respective mechanisms could significantly accelerate clot dissolution Therefore, ultrasound catheter systems configured for use with a combined microbubble and therapeutic compound have been developed.

In one embodiment of the present invention, a method of treating a vascular occlusion located at a treatment site within a patient's vasculature comprises positioning an ultrasound catheter at the treatment site. The method further comprises delivering a combination compound consisting of microbubbles and therapeutic agents (i.e., microbubble-therapeutic compound) from an ultrasound catheter to the vascular occlusion and delivering ultrasonic energy from the ultrasound assembly to the vascular occlusion concurrently. The microbubble-therapeutic compound having an original microbubble concentration is diluted to less than or equal to approximately 1% by volume at the deliverance to the catheter, or alternatively, the microbubble-therapeutic compound has an effective microbubble concentration of less than or equal to approximately 0.01% of the original microbubble concentration at deliverance into the vascular occlusion when the ultrasound transducer is emitting.

In one embodiment of the present invention, a method of treating a vascular occlusion located at a treatment site within a patient's vasculature comprises passing an ultrasound catheter through the patient's vasculature to the treatment site. The ultrasound catheter includes at least one distal fluid delivery port and at least one ultrasound radiating member. The method further comprises delivering a microbubble-therapeutic compound having an initial microbubble concentration delivered from the proximal fluid delivery port into the vascular occlusion after passing the not acoustically isolated tip, and delivering ultrasonic energy from the ultrasound assembly to the vascular occlusion concurrent to delivering the microbubble-therapeutic compound. The microbubble-therapeutic compound has an effective microbubble concentration at the point of delivery to the vascular occlusion of about 1% of the initial microbubble concentration In some embodiments, the method further comprises positioning the ultrasound catheter at the treatment site such that the at least one fluid delivery port is positioned within the occlusion. In some embodiments, the method may further comprise continuous infusion of a combined microbubble-therapeutic compound from the ultrasound catheter into an internal portion of the occlusion. The method further comprises repositioning the ultrasound catheter at the treatment site. In one embodiment of the present invention, an ultrasound catheter system comprises an elongate tubular body having an ultrasound radiating member and a fluid delivery lumen positioned therein. The system further comprises a fluid reservoir that is hydraulically coupled to a proximal portion of the fluid delivery lumen. The fluid delivery reservoir contains a combined microbubble-therapeutic compound. The system further comprises an infusion pump configured to pump the microbubble-therapeutic compound from the fluid reservoir into the fluid delivery lumen.

BRIEF DESCRIPTION OF THE DRAWINGS

Exemplary embodiments of the vascular occlusion treatment system are illustrated in the accompanying drawings, which are for illustrative purposes only. The drawings comprise the following figures, in which like numerals indicate like parts.

FIG. 7A is a schematic illustration of the ultrasound assembly of FIG. 5 housed within the inner core of FIG. 4.

FIG. 8 illustrates the energy delivery section of the inner core of FIG. 4 positioned within the energy delivery section of the tubular body of FIG. 2.

FIG. 11B is a side view of the distal end of an ultrasonic catheter positioned at the treatment site of FIG. 11A.

FIG. 11D is a cross-sectional view of the distal end of the ultrasonic catheter of FIG. 11C, wherein an inner core has been inserted into the tubular body to perform a treatment.

FIG. 12A is a cross-sectional view of a distal end of an ultrasonic catheter configured for use within small vessels of a patient's vasculature.

FIG. 12B is a cross-sectional view of the ultrasonic catheter of FIG. 12A taken through line 12B-12B.

DETAILED DESCRIPTION OF PREFERRED EMBODIMENTS

Figure 1:
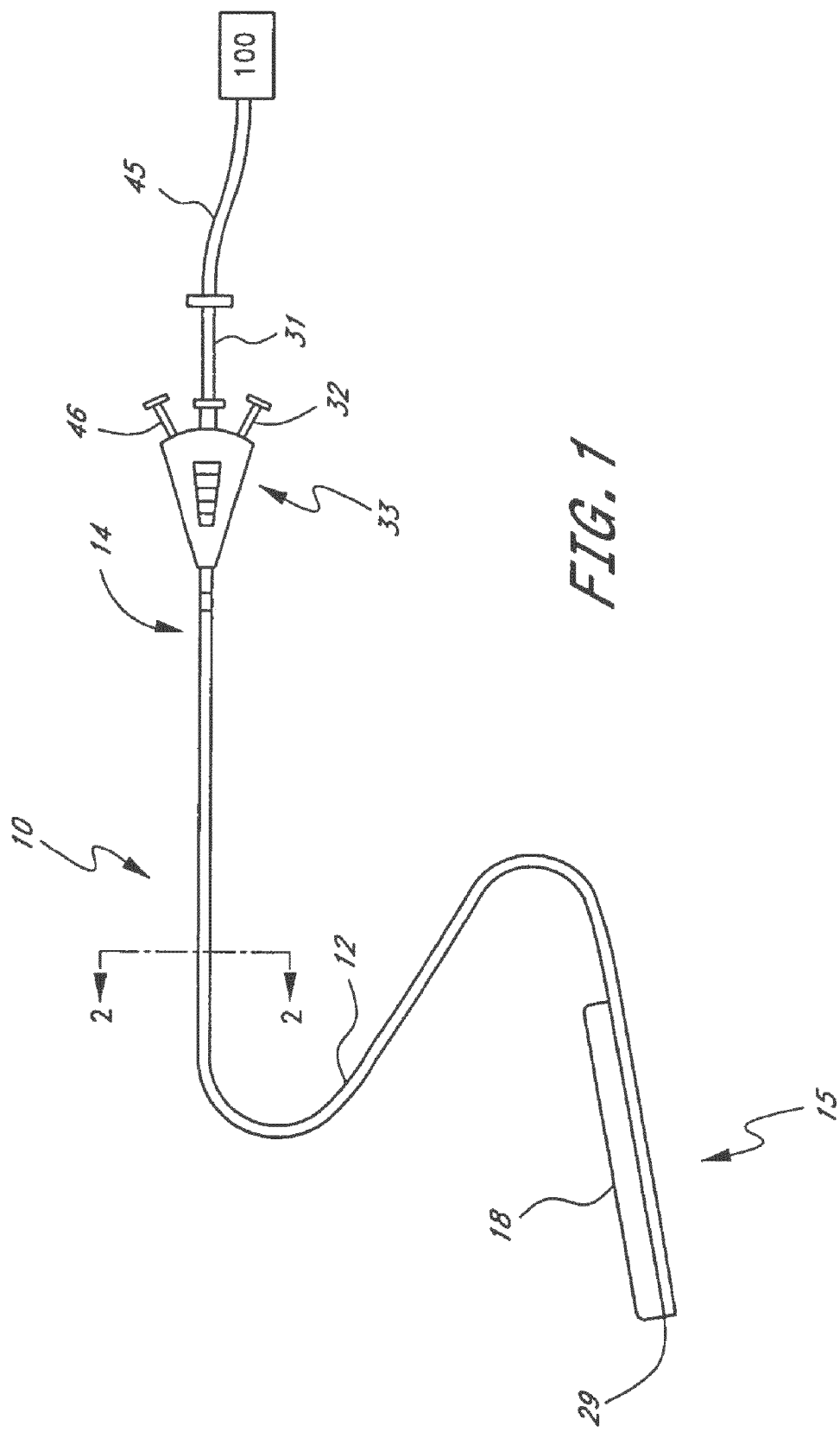
FIG. 1 is a schematic illustration of an ultrasonic catheter configured for insertion into large vessels of the human body.

As set forth above, methods and apparatuses have been developed that allow a vascular occlusion to be treated using both ultrasonic energy and a combined microbubbles-therapeutic compound. Disclosed herein are several exemplary embodiments of ultrasonic catheters that can be used to enhance the efficacy of therapeutic compounds at a treatment site within a patient's body. Also disclosed are exemplary methods for using such catheters.

Introduction

As used herein, the term "therapeutic compound" refers broadly, without limitation, and in addition to its ordinary meaning, to a drug, medicament, dissolution compound, genetic material or any other substance capable of effecting physiological functions. Additionally, a mixture that includes substances such as these is also encompassed within this definition of "therapeutic compound". Examples of therapeutic compounds include thrombolytic compounds, anti-thrombosis compounds, sonosensetizer compounds, gene, protein and/or stem cell compounds and other compounds used in the treatment of vasculature, including compounds intended to prevent or reduce clot formation. In applications where human blood vessels that have become partially or completely occluded by plaque, thrombi, emboli or other substances that reduce the blood carrying capacity of a vessel, exemplary therapeutic compounds include, but are not limited to, heparin, urokinase, streptokinase, tPA, rtPA, Retevase and Tenecteplase.

As used herein, the terms "ultrasonic energy", "ultrasound" and "ultrasonic" refer broadly, without limitation, and in addition to their ordinary meaning, to mechanical energy transferred through longitudinal pressure or compression waves. Ultrasonic energy can be emitted as continuous or pulsed waves, depending on the parameters of a particular application. Additionally, ultrasonic energy can be emitted in waveforms having various shapes, such as sinusoidal waves, triangle waves, square waves, or other wave forms. Ultrasonic energy includes sound waves. In certain embodiments, the ultrasonic energy referred to herein has a frequency between about 20 kHz and about 20 MHz. For example, in one embodiment, the ultrasonic energy has a frequency between about 500 kHz and about 20 MHz. In another embodiment, the ultrasonic energy has a frequency between about 1 MHz and about 3 MHz. In yet another embodiment, the ultrasonic energy has a frequency of about 2 MHz. In certain embodiments described herein, the time average acoustic power of the ultrasonic energy is between about 0.01 watts and 3 watts per ultrasound transducer. In one embodiment, the time average acoustic power is between 0.1 to 1 watts per ultrasound transducer. In one embodiment, the time average acoustic power is about 0.45 watts per ultrasound transducer.

As used herein, the term "ultrasound radiating member" refers broadly, without limitation, and in addition to its ordinary meaning, to any apparatus capable of producing ultrasonic energy. An ultrasonic transducer, which converts electrical energy into ultrasonic energy, is an example of an ultrasound radiating member. An exemplary ultrasonic transducer capable of generating ultrasonic energy from electrical energy is a piezoelectric ceramic oscillator. Piezoelectric ceramics typically comprise a crystalline material, such as quartz, that changes shape when an electrical current is applied to the material. This change in shape, made oscillatory by an oscillating driving signal, creates ultrasonic sound waves. In other embodiments, ultrasonic energy can be generated by an ultrasonic transducer that is remote from the ultrasound radiating member, and the ultrasonic energy can be transmitted, via, for example, a wire that is coupled to the ultrasound radiating member.

In certain applications, the ultrasonic energy itself provides a therapeutic effect to the patient. Examples of such therapeutic effects include preventing or reducing stenosis and/or restenosis; tissue ablation, abrasion or disruption; promoting temporary or permanent physiological changes in intracellular or intercellular structures; and rupturing micro-balloons or micro-bubbles for therapeutic compound delivery. Further information about such methods can be found in U.S. Pat. Nos. 5,261,291 and 5,431,663.

The ultrasonic catheters described herein can be configured for application of ultrasonic energy over a substantial length of a body lumen, such as, for example, the larger vessels located in the leg. In other embodiments, the ultrasonic catheters described herein can be configured to be inserted into the small cerebral vessels, in solid tissues, in duct systems and in body cavities. Additional embodiments that can be combined with certain features and aspects of the embodiments described herein are described in U.S. patent application Ser. No. 10/291,891, filed 7 Nov. 2002, the entire disclosure of which is hereby incorporated herein by reference.

Overview of a Large Vessel Ultrasonic Catheter

FIG. 1 schematically illustrates an ultrasonic catheter 10 configured for use in the large vessels of a patient's anatomy. For example, the ultrasonic catheter 10 illustrated in FIG. 1 can be used to treat long segment peripheral arterial occlusions, such as those in the vascular system of the leg.

As illustrated in FIG. 1, the ultrasonic catheter 10 generally includes a multi-component, elongate flexible tubular body 12 having a proximal region 14 and a distal region 15. The tubular body 12 includes a flexible energy delivery section 18 located in the distal region 15. The tubular body 12 and other components of the catheter 10 can be manufactured in accordance with a variety of techniques known to an ordinarily skilled artisan. Suitable materials and dimensions can be readily selected based on the natural and anatomical dimensions of the treatment site and on the desired percutaneous access site.

For example, in an exemplary embodiment, the tubular body proximal region 14 comprises a material that has sufficient flexibility, kink resistance, rigidity and structural support to push the energy delivery section 18 through the patient's vasculature to a treatment site. Examples of such materials include, but are not limited to, extruded polytetrafluoroethylene ("PTFE"), polyethylenes ("PE"), polyamides and other similar materials. In certain embodiments, the tubular body proximal region 14 is reinforced by braiding, mesh or other constructions to provide increased kink resistance and ability to be pushed. For example, nickel titanium or stainless steel wires can be placed along or incorporated into the tubular body 12 to reduce kinking.

For example, in an embodiment configured for treating thrombus in the arteries of the leg, the tubular body 12 has an outside diameter between about 0.060 inches and about 0.075 inches. In another embodiment, the tubular body 12 has an outside diameter of about 0.071 inches. In certain embodiments, the tubular body 12 has an axial length of approximately 105 centimeters, although other lengths can be used in other applications.

In an exemplary embodiment, the tubular body energy delivery section 18 comprises a material that is thinner than the material comprising the tubular body proximal region 14. In another exemplary embodiment, the tubular body energy delivery section 18 comprises a material that has a greater acoustic transparency than the material comprising the tubular body proximal region 14. Thinner materials generally have greater acoustic transparency than thicker materials. Suitable materials for the energy delivery section 18 include, but are not limited to, high or low density polyethylenes, urethanes, nylons, and the like. In certain modified embodiments, the energy delivery section 18 comprises the same material or a material of the same thickness as the proximal region 18.

In an exemplary embodiment, the tubular body 12 is divided into at least three sections of varying stiffness. The first section, which includes the proximal region 14, has a relatively higher stiffness. The second section, which is located in an intermediate region between the proximal region 14 and the distal region 15, has a relatively lower stiffness. This configuration further facilitates movement and placement of the catheter 10. The third section, which includes the energy delivery section 18, has a relatively lower stiffness than the second section in spite of the presence of ultrasound radiating members which can be positioned therein.

Figure 2:
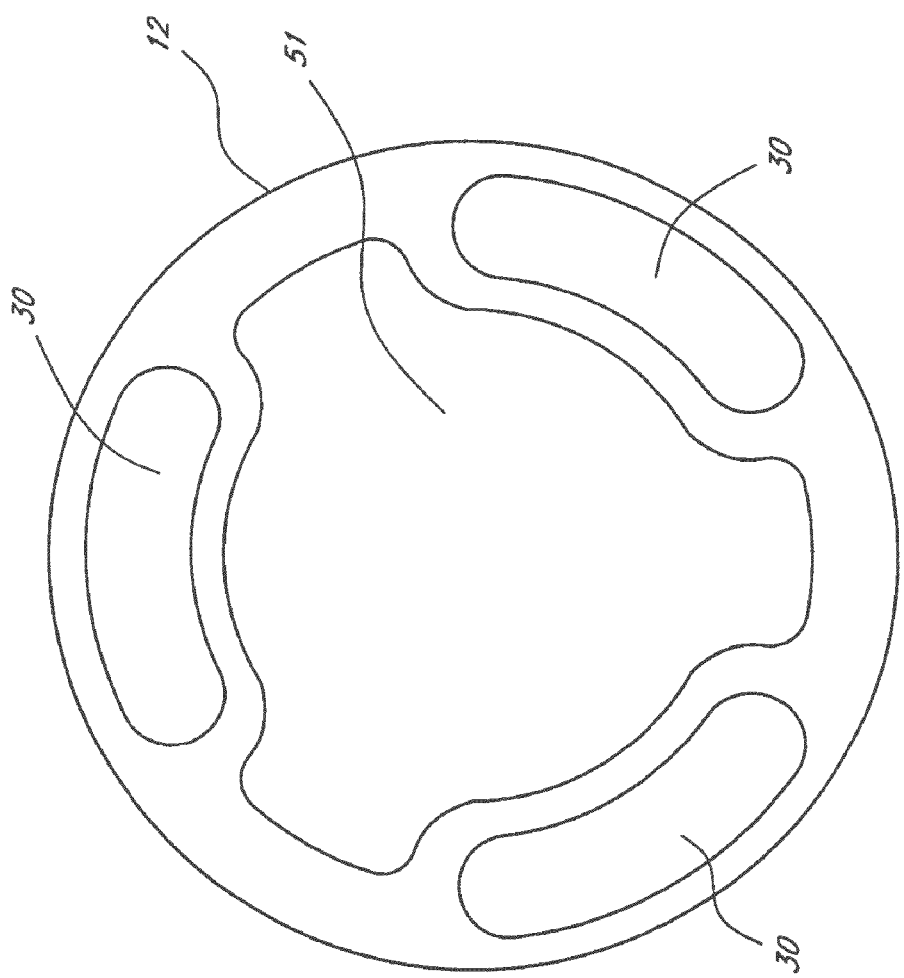
FIG. 2 is a cross-sectional view of the ultrasonic catheter of FIG. 1 taken along line 2-2.

FIG. 2 illustrates a cross section of the tubular body 12 taken along line 2-2 in FIG. 1. In the embodiment illustrated in FIG. 2, three fluid delivery lumens 30 are incorporated into the tubular body 12. In other embodiments, more or fewer fluid delivery lumens can be incorporated into the tubular body 12. In such embodiments, the arrangement of the fluid delivery lumens 30 provides a hollow central lumen 51 passing through the tubular body 12. The cross-section of the tubular body 12, as illustrated in FIG. 2, is substantially constant along the length of the catheter 10. Thus, in such embodiments, substantially the same cross-section is present in both the proximal region 14 and the distal region 15 of the tubular body 12, including the energy delivery section 18.

In certain embodiments, the central lumen 51 has a minimum diameter greater than about 0.030 inches. In another embodiment, the central lumen 51 has a minimum diameter greater than about 0.037 inches. In an exemplary embodiment, the fluid delivery lumens 30 have dimensions of about 0.026 inches wide by about 0.0075 inches high, although other dimensions can be used in other embodiments.

In an exemplary embodiment, the central lumen 51 extends through the length of the tubular body 12. As illustrated in FIG. 1, the central lumen 51 has a distal exit port 29 and a proximal access port 31. The proximal access port 31 forms part of the backend hub 33, which is attached to the tubular body proximal region 14. In such embodiments, the backend hub also includes a cooling fluid fitting 46, which is hydraulically connected to the central lumen 51. In such embodiments, the backend hub 33 also includes a therapeutic compound inlet port 32, which is hydraulically coupled to the fluid delivery lumens 30, and which can also be hydraulically coupled to a source of therapeutic compound via a hub such as a Luer fitting.

Figure 3:
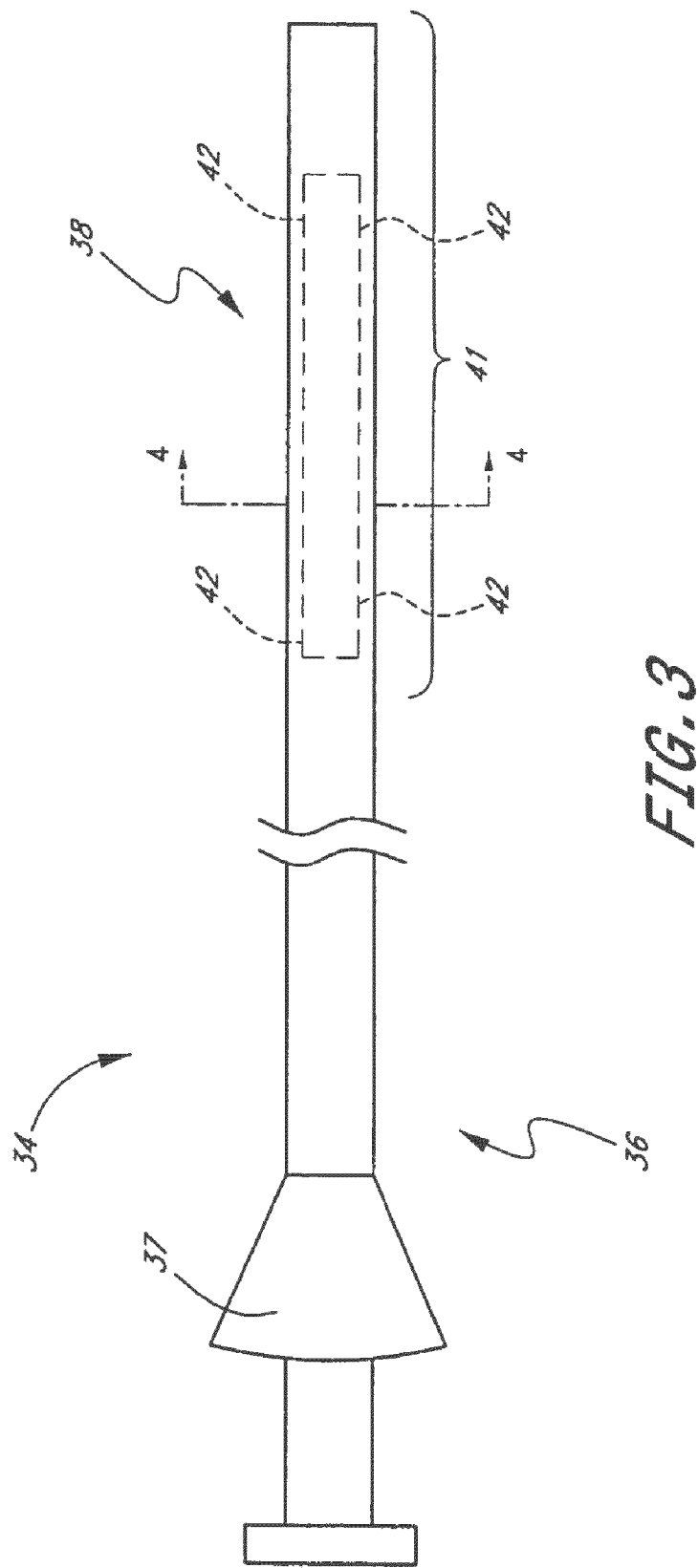
FIG. 3 is a schematic illustration of an elongate inner core configured to be positioned within the central lumen of the catheter illustrated in FIG. 2.

The central lumen 51 is configured to receive an elongate inner core 34, an exemplary embodiment of which is illustrated in FIG. 3. In such embodiments, the elongate inner core 34 includes a proximal region 36 and a distal region 38. A proximal hub 37 is fitted on one end of the inner core proximal region 36. One or more ultrasound radiating members 40 are positioned within an inner core energy delivery section 41 that is located within the distal region 38. The ultrasound radiating members 40 form an ultrasound assembly 42, which will be described in greater detail below.

Figure 4:
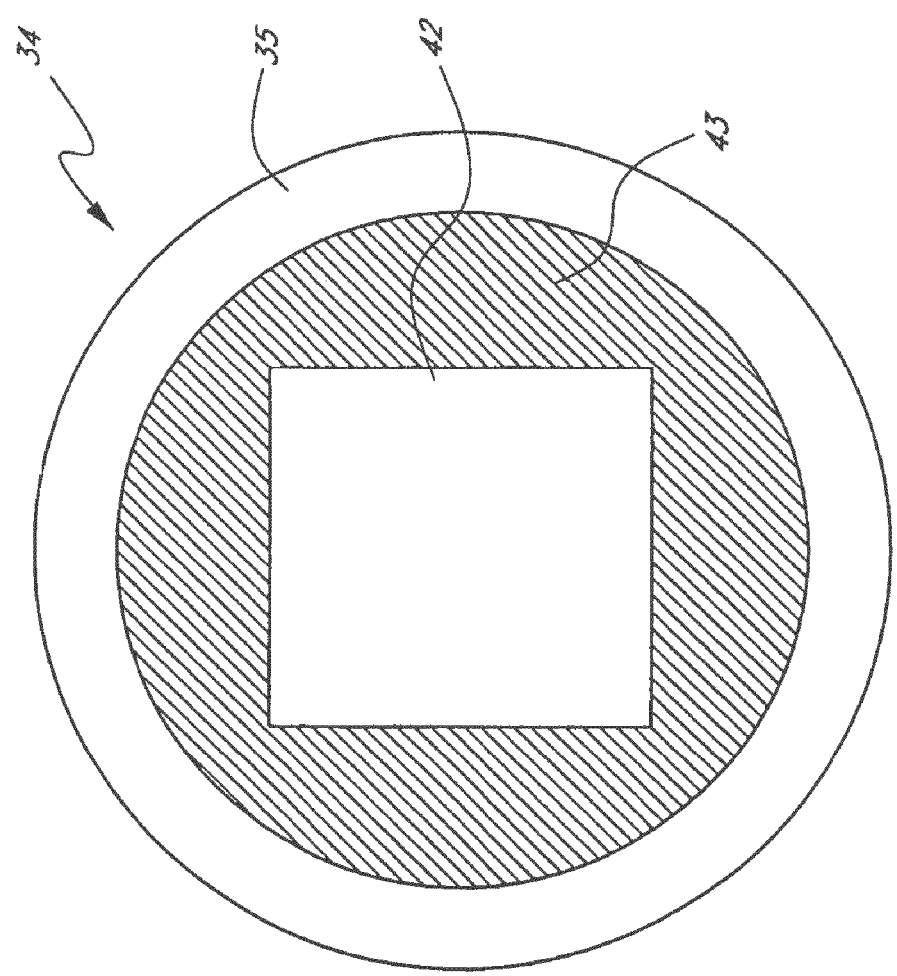
FIG. 4 is a cross-sectional view of the elongate inner core of FIG. 3 taken along line 4-4.

As shown in the cross-section illustrated in FIG. 4, which is taken along lines 4-4 in FIG. 3, in an exemplary embodiment, the inner core 34 has a cylindrical shape, with an outer diameter that permits the inner core 34 to be inserted into the central lumen 51 of the tubular body 12 via the proximal access port 31. Suitable outer diameters of the inner core 34 include, but are not limited to, between about 0.010 inches and about 0.100 inches. In another embodiment, the outer diameter of the inner core 34 is between about 0.020 inches and about 0.080 inches. In yet another embodiment, the inner core 34 has an outer diameter of about 0.035 inches.

Still referring to FIG. 4, the inner core 34 includes a cylindrical outer body 35 that houses the ultrasound assembly 42. The ultrasound assembly 42 includes wiring and ultrasound radiating members, described in greater detail in FIGS. 5 through 7D, such that the ultrasound assembly 42 is capable of radiating ultrasonic energy from the energy delivery section 41 of the inner core 34. The ultrasound assembly 42 is electrically connected to the backend hub 33, where the inner core 34 can be connected to a control system 100 via cable 45 (illustrated in FIG. 1). In an exemplary embodiment, an electrically insulating potting material 43 fills the inner core 34, surrounding the ultrasound assembly 42, thus reducing or preventing movement of the ultrasound assembly 42 with respect to the outer body 35. In one embodiment, the thickness of the outer body 35 is between about 0.0002 inches and 0.010 inches. In another embodiment, the thickness of the outer body 35 is between about 0.0002 inches and 0.005 inches. In yet another embodiment, the thickness of the outer body 35 is about 0.0005 inches.

Figure 5:
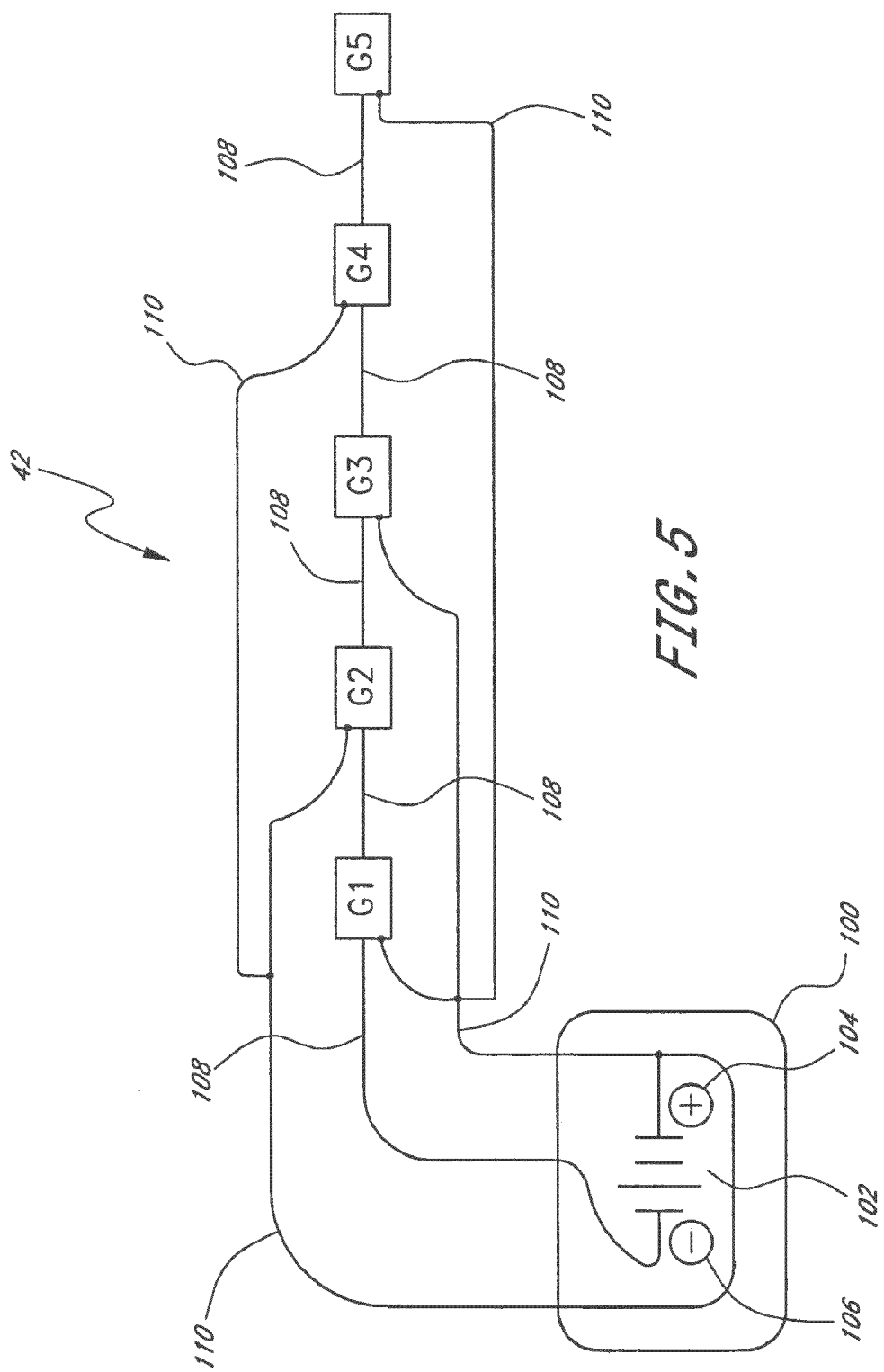
FIG. 5 is a schematic wiring diagram illustrating an exemplary technique for electrically connecting five groups of ultrasound radiating members to form an ultrasound assembly.
Figure 6:
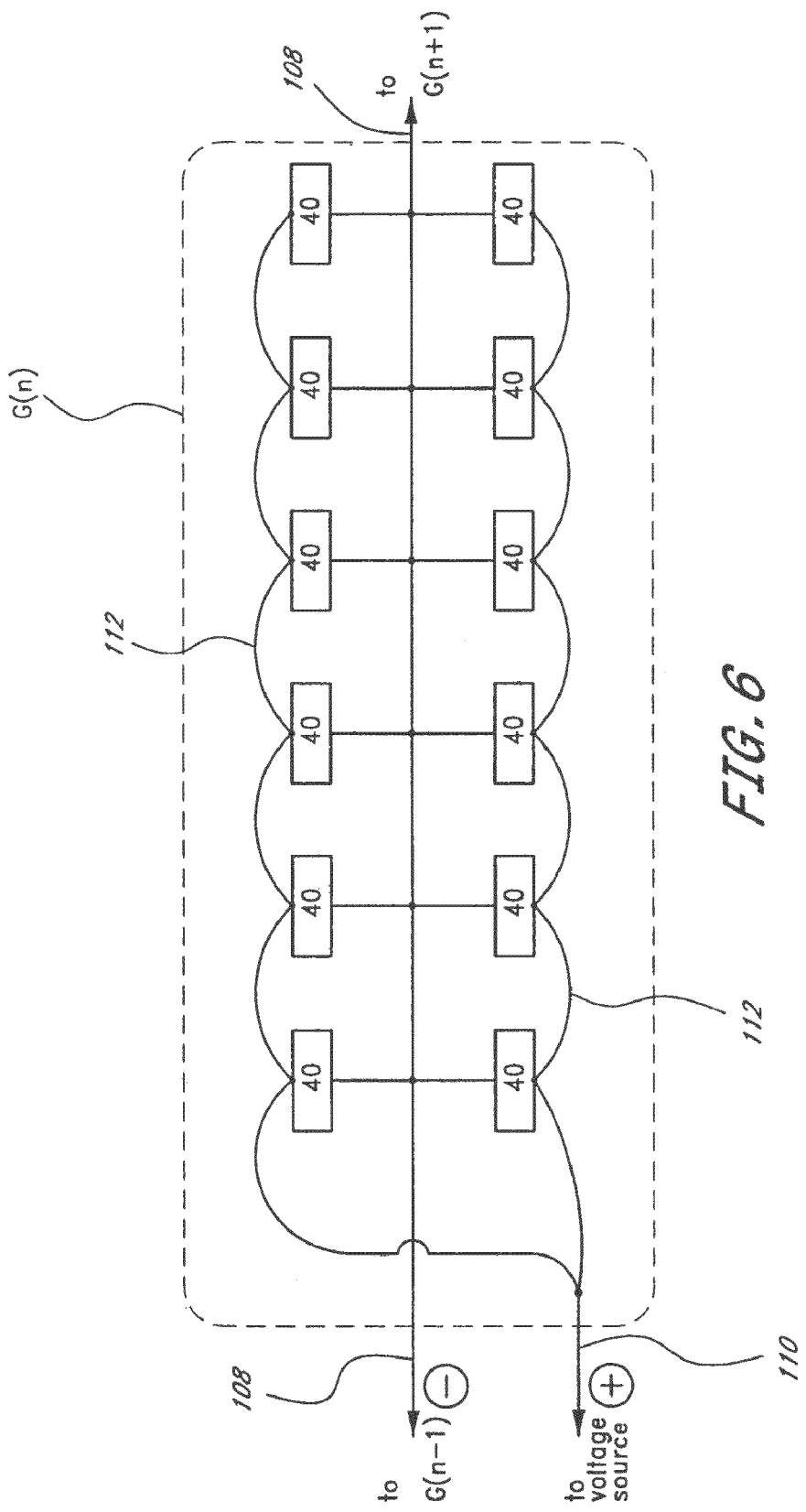
FIG. 6 is a schematic wiring diagram illustrating an exemplary technique for electrically connecting one of the groups of FIG. 5.

In an exemplary embodiment, the ultrasound assembly 42 includes a plurality of ultrasound radiating members 40 that are divided into one or more groups. For example, FIGS. 5 and 6 are schematic wiring diagrams illustrating one technique for connecting five groups of ultrasound radiating members 40 to form the ultrasound assembly 42. As illustrated in FIG. 5, the ultrasound assembly 42 comprises five groups G1, G2, G3, G4, G5 of ultrasound radiating members 40 that are electrically connected to each other. The five groups are also electrically connected to the control system 100.

Still referring to FIG. 5, in an exemplary embodiment, the control circuitry 100 includes a voltage source 102 having a positive terminal 104 and a negative terminal 106. The negative terminal 106 is connected to common wire 108, which connects the five groups G1-G5 of ultrasound radiating members 40 in series. The positive terminal 104 is connected to a plurality of lead wires 110, which each connect to one of the five groups G1-G5 of ultrasound radiating members 40. Thus, under this configuration, each of the five groups G1-G5, one of which is illustrated in FIG. 6, is connected to the positive terminal 104 via one of the lead wires 110, and to the negative terminal 106 via the common wire 108.

Referring now to FIG. 6, each group G1-G5 includes a plurality of ultrasound radiating members 40. Each of the ultrasound radiating members 40 is electrically connected to the common wire 108 and to the lead wire 110 via a positive contact wires 112. Thus, when wired as illustrated, a substantially constant voltage difference will be applied to each ultrasound radiating member 40 in the group. Although the group illustrated in FIG. 6 includes twelve ultrasound radiating members 40, in other embodiments, more or fewer ultrasound radiating members 40 can be included in the group. Likewise, more or fewer than five groups can be included within the ultrasound assembly 42 illustrated in FIG. 5.

FIG. 7A illustrates an exemplary technique for arranging the components of the ultrasound assembly 42 (as schematically illustrated in FIG. 5) into the inner core 34 (as schematically illustrated in FIG. 4). FIG. 7A is a cross-sectional view of the ultrasound assembly 42 taken within group G1 in FIG. 5, as indicated by the presence of four lead wires 110. For example, if a cross-sectional view of the ultrasound assembly 42 was taken within group G4 in FIG. 5, only one lead wire 110 would be present (that is, the one lead wire connecting group G5).

In the exemplary embodiment illustrated in FIG. 7A, the common wire 108 includes an elongate, flat piece of electrically conductive material in electrical contact with a pair of ultrasound radiating members 40. Each of the ultrasound radiating members 40 is also in electrical contact with a positive contact wire 112. Because the common wire 108 is connected to the negative terminal 106, and the positive contact wire 112 is connected to the positive terminal 104, a voltage difference can be created across each ultrasound radiating member 40. In such embodiments, lead wires 110 are separated from the other components of the ultrasound assembly 42, thus preventing interference with the operation of the ultrasound radiating members 40 as described above. For example, in an exemplary embodiment, the inner core 34 is filled with an insulating potting material 43, thus deterring unwanted electrical contact between the various components of the ultrasound assembly 42.

Figure 7B:
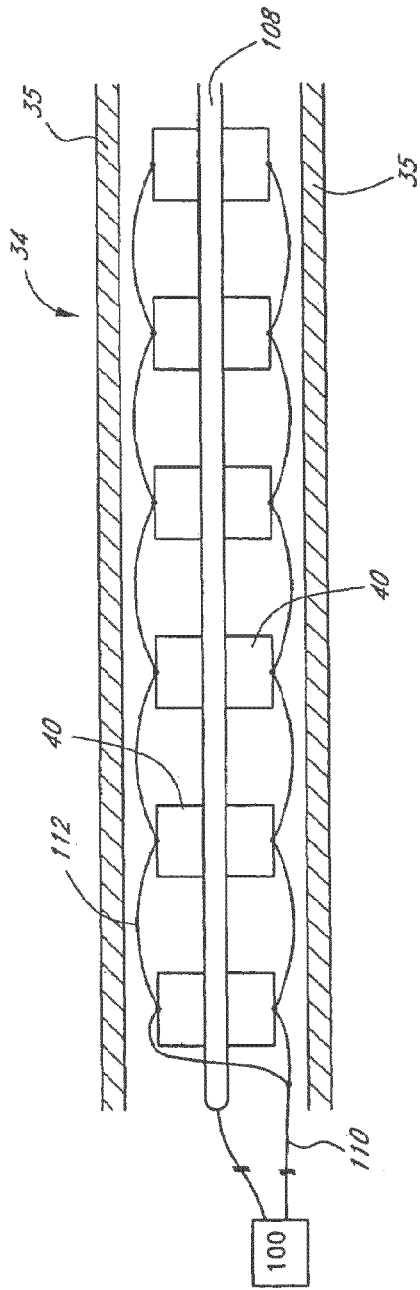
FIG. 7B is a cross-sectional view of the ultrasound assembly of FIG. 7A taken along line 7B-7B.
Figure 7C:
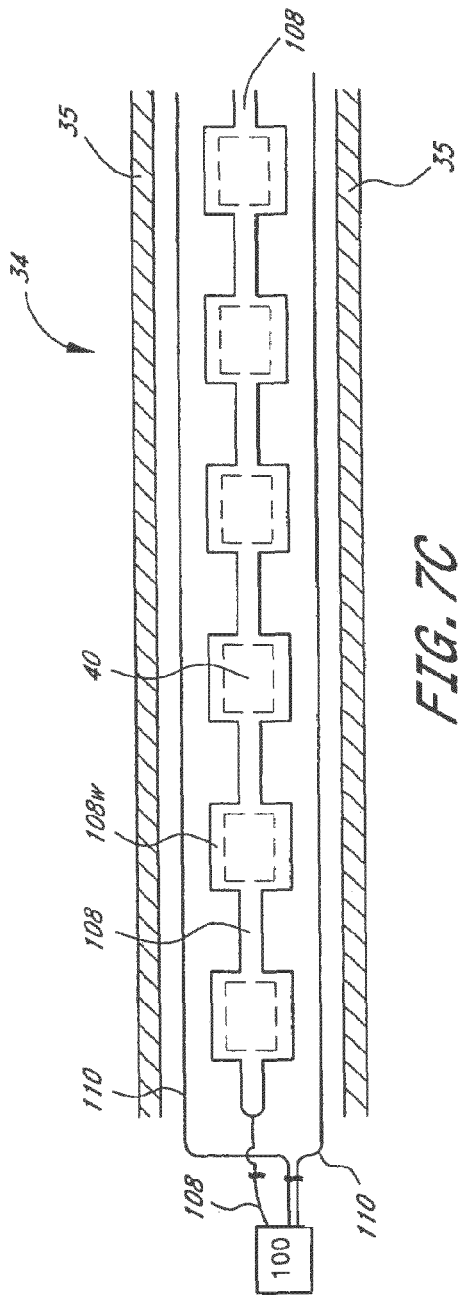
FIG. 7C is a cross-sectional view of the ultrasound assembly of FIG. 7A taken along line 7C-7C.

FIGS. 7B and 7C illustrate cross sectional views of the inner core 34 of FIG. 7A taken along lines 7B-7B and 7C-7C, respectively. As illustrated in FIG. 7B, the ultrasound radiating members 40 are mounted in pairs along the common wire 108. The ultrasound radiating members 40 are connected by positive contact wires 112, such that substantially the same voltage is applied to each ultrasound radiating member 40. As illustrated in FIG. 7C, the common wire 108 includes wide regions 108W upon which the ultrasound radiating members 40 can be mounted, thus reducing the likelihood that the paired ultrasound radiating members 40 will short together. In certain embodiments, outside the wide regions 108W, the common wire 108 can have a more conventional, rounded wire shape.

Figure 7D:
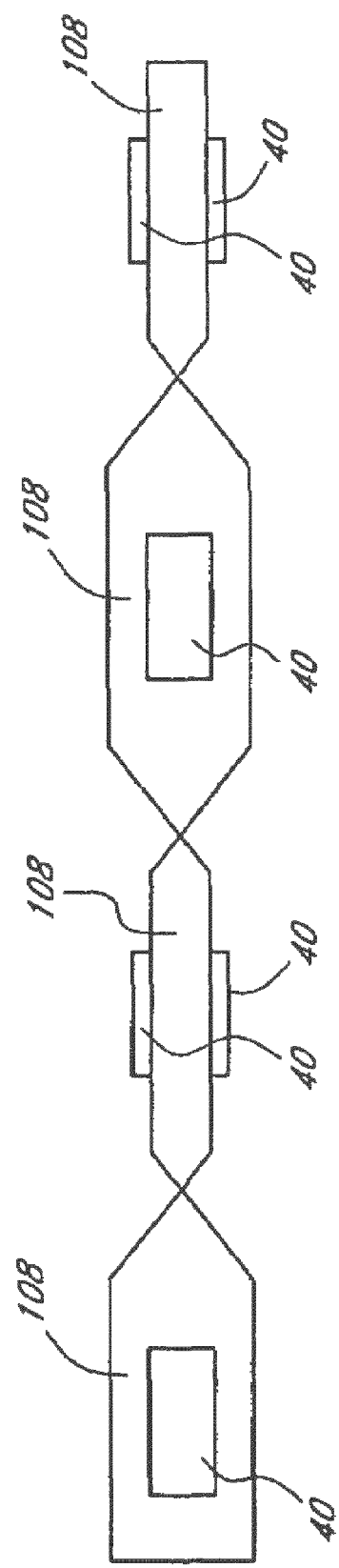
FIG. 7D is a side view of an ultrasound assembly center wire twisted into a helical configuration.

In a modified embodiment, such as illustrated in FIG. 7D, the common wire 108 is twisted to form a helical shape before being fixed within the inner core 34. In such embodiments, the ultrasound radiating members 40 are oriented in a plurality of radial directions, thus enhancing the radial uniformity of the resulting ultrasonic energy field.

The wiring arrangement described above can be modified to allow each group G1, G2, G3, G4, G5 to be independently powered. Specifically, by providing a separate power source within the control system 100 for each group, each group can be individually turned on or off, or can be driven at an individualized power level. This advantageously allows the delivery of ultrasonic energy to be "turned off" in regions of the treatment site where treatment is complete, thus preventing deleterious or unnecessary ultrasonic energy to be applied to the patient.

The embodiments described above, and illustrated in FIGS. 5 through 7, include a plurality of ultrasound radiating members grouped spatially. That is, in such embodiments, the ultrasound radiating members within a certain group are positioned adjacent to each other, such that when a single group is activated, ultrasonic energy is delivered from a certain length of the ultrasound assembly. However, in modified embodiments, the ultrasound radiating members of a certain group may be spaced apart from each other, such that the ultrasound radiating members within a certain group are not positioned adjacent to each other. In such embodiments, when a single group is activated, ultrasonic energy can be delivered from a larger, spaced apart portion of the ultrasound assembly. Such modified embodiments can be advantageous in applications where a less focused, more diffuse ultrasonic energy field is to be delivered to the treatment site.

In an exemplary embodiment, the ultrasound radiating members 40 comprise rectangular lead zirconate titanate ("PZT") ultrasound transducers that have dimensions of about 0.017 inches by about 0.010 inches by about 0.080 inches. In other embodiments, other configurations and dimensions can be used. For example, disc-shaped ultrasound radiating members 40 can be used in other embodiments. In an exemplary embodiment, the common wire 108 comprises copper, and is about 0.005 inches thick, although other electrically conductive materials and other dimensions can be used in other embodiments. In an exemplary embodiment, lead wires 110 are 36 gauge electrical conductors, and positive contact wires 112 are 42 gauge electrical conductors. However, other wire gauges can be used in other embodiments.

As described above, suitable frequencies for the ultrasound radiating members 40 include, but are not limited to, from about 20 kHz to about 20 MHz. In one embodiment, the frequency is between about 500 kHz and about 20 MHz, and in another embodiment the frequency is between about 1 MHz and about 3 MHz. In yet another embodiment, the ultrasound radiating members 40 are operated with a frequency of about 2 MHz.

FIG. 8 illustrates the inner core 34 positioned within the tubular body 12. Details of the ultrasound assembly 42, provided in FIG. 7A, are omitted for clarity. As described above, the inner core 34 can be slid within the central lumen 51 of the tubular body 12, thereby allowing the inner core energy delivery section 41 to be positioned within the tubular body energy delivery section 18. For example, in an exemplary embodiment, the materials comprising the inner core energy delivery section 41, the tubular body energy delivery section 18, and the potting material 43 all comprise materials having a similar acoustic impedance, thereby minimizing ultrasonic energy losses across material interfaces.

FIG. 8 further illustrates placement of fluid delivery ports 58 within the tubular body energy delivery section 18. As illustrated, holes or slits are formed from the fluid delivery lumen 30 through the tubular body 12, thereby permitting fluid flow from the fluid delivery lumen 30 to the treatment site. A plurality of fluid delivery ports 58 can be positioned axially along the tubular body 12. Thus, a source of therapeutic compound coupled to the inlet port 32 provides a hydraulic pressure which drives the therapeutic compound through the fluid delivery lumens 30 and out the fluid delivery ports 58.

By spacing the fluid delivery lumens 30 around the circumference of the tubular body 12 substantially evenly, as illustrated in FIG. 8, a substantially uniform flow of therapeutic compound around the circumference of the tubular body 12 can be achieved. Additionally, the size, location and geometry of the fluid delivery ports 58 can be selected to provide uniform fluid flow from the fluid delivery ports 30 to the treatment site. For example, in one embodiment, fluid delivery ports closer to the proximal region of the energy delivery section 18 have smaller diameters than fluid delivery ports closer to the distal region of the energy delivery section 18, thereby allowing uniform delivery of therapeutic compound in the energy delivery section.

For example, in one embodiment in which the fluid delivery ports 58 have similar sizes along the length of the tubular body 12, the fluid delivery ports 58 have a diameter between about 0.0005 inches to about 0.0050 inches. In another embodiment in which the size of the fluid delivery ports 58 changes along the length of the tubular body 12, the fluid delivery ports 58 have a diameter between about 0.001 inches to about 0.005 inches in the proximal region of the energy delivery section 18, and between about 0.005 inches to about 0.0020 inches in the distal region of the energy delivery section 18. The increase in size between adjacent fluid delivery ports 58 depends on a variety of factors, including the material comprising the tubular body 12, and on the size of the fluid delivery lumen 30. The fluid delivery ports 58 can be created in the tubular body 12 by punching, drilling, burning or ablating (such as with a laser), or by other suitable methods. Therapeutic compound flow along the length of the tubular body 12 can also be increased by increasing the density of the fluid delivery ports 58 toward the distal region of the energy delivery section.

In certain applications, a spatially nonuniform flow of therapeutic compound from the fluid delivery ports 58 to the treatment site is to be provided. In such applications, the size, location and geometry of the fluid delivery ports 58 can be selected to provide such nonuniform fluid flow.

Referring still to FIG. 8, placement of the inner core 34 within the tubular body 12 further defines cooling fluid lumens 44. Cooling fluid lumens 44 are formed between an outer surface 39 of the inner core 34 and an inner surface 16 of the tubular body 12. In certain embodiments, a cooling fluid is introduced through the proximal access port 31 such that cooling fluid flows through cooling fluid lumens 44 and out of the catheter 10 through distal exit port 29 (see FIG. 1). In an exemplary embodiment, the cooling fluid lumens 44 are substantially evenly spaced around the circumference of the tubular body 12 (that is, at approximately 120° increments for a three-lumen configuration), thereby providing substantially uniform cooling fluid flow over the inner core 34. Such a configuration advantageously removes thermal energy from the treatment site. As will be explained below, the flow rate of the cooling fluid and the power to the ultrasound assembly 42 can be adjusted to maintain the temperature of the inner core energy delivery section 41, or of the treatment site generally, within a desired range.

In an exemplary embodiment, the inner core 34 can be rotated or moved within the tubular body 12. Specifically, movement of the inner core 34 can be accomplished by maneuvering the proximal hub 37 while holding the backend hub 33 stationary. The inner core outer body 35 is at least partially constructed from a material that provides enough structural support to permit movement of the inner core 34 within the tubular body 12 without kinking of the tubular body 12. Additionally, in an exemplary embodiment, the inner core outer body 35 comprises a material having the ability to transmit torque. Suitable materials for the inner core outer body 35 include, but are not limited to, polyimides, polyesters, polyurethanes, thermoplastic elastomers and braided polyimides.

In an exemplary embodiment, the fluid delivery lumens 30 and the cooling fluid lumens 44 are open at the distal end of the tubular body 12, thereby allowing the therapeutic compound and the cooling fluid to pass into the patient's vasculature at the distal exit port 29. In a modified embodiment, the fluid delivery lumens 30 can be selectively occluded at the distal end of the tubular body 12, thereby providing additional hydraulic pressure to drive the therapeutic compound out of the fluid delivery ports 58. In either configuration, the inner core 34 can be prevented from passing through the distal exit port 29 by providing the inner core 34 with a length that is less than the length of the tubular body 12. In other embodiments, a protrusion is formed within the tubular body 12 in the distal region 15, thereby preventing the inner core 34 from passing through the distal exit port 29.

In other embodiments, the catheter 10 includes an occlusion device positioned at the distal exit port 29. In such embodiments, the occlusion device has a reduced inner diameter that can accommodate a guidewire, but that is less than the inner diameter of the central lumen 51. Thus, the inner core 34 is prevented from extending past the occlusion device and out the distal exit port 29. For example, suitable inner diameters for the occlusion device include, but are not limited to, between about 0.005 inches and about 0.050 inches. In other embodiments, the occlusion device has a closed end, thus preventing cooling fluid from leaving the catheter 10, and instead recirculating to the tubular body proximal region 14. These and other cooling fluid flow configurations permit the power provided to the ultrasound assembly 42 to be increased in proportion to the cooling fluid flow rate. Additionally, certain cooling fluid flow configurations can reduce exposure of the patient's body to cooling fluids.

In an exemplary embodiment, such as illustrated in FIG. 8, the tubular body 12 includes one or more temperature sensors 20 that are positioned within the energy delivery section 18. In such embodiments, the tubular body proximal region 14 includes a temperature sensor lead which can be incorporated into cable 45 (illustrated in FIG. 1). Suitable temperature sensors include, but are not limited to, temperature sensing diodes, thermistors, thermocouples, resistance temperature detectors ("RTDs") and fiber optic temperature sensors which use thermalchromic liquid crystals. Suitable temperature sensor 20 geometries include, but are not limited to, a point, a patch or a stripe. The temperature sensors 20 can be positioned within one or more of the fluid delivery lumens 30, and/or within one or more of the cooling fluid lumens 44.

Figure 9:
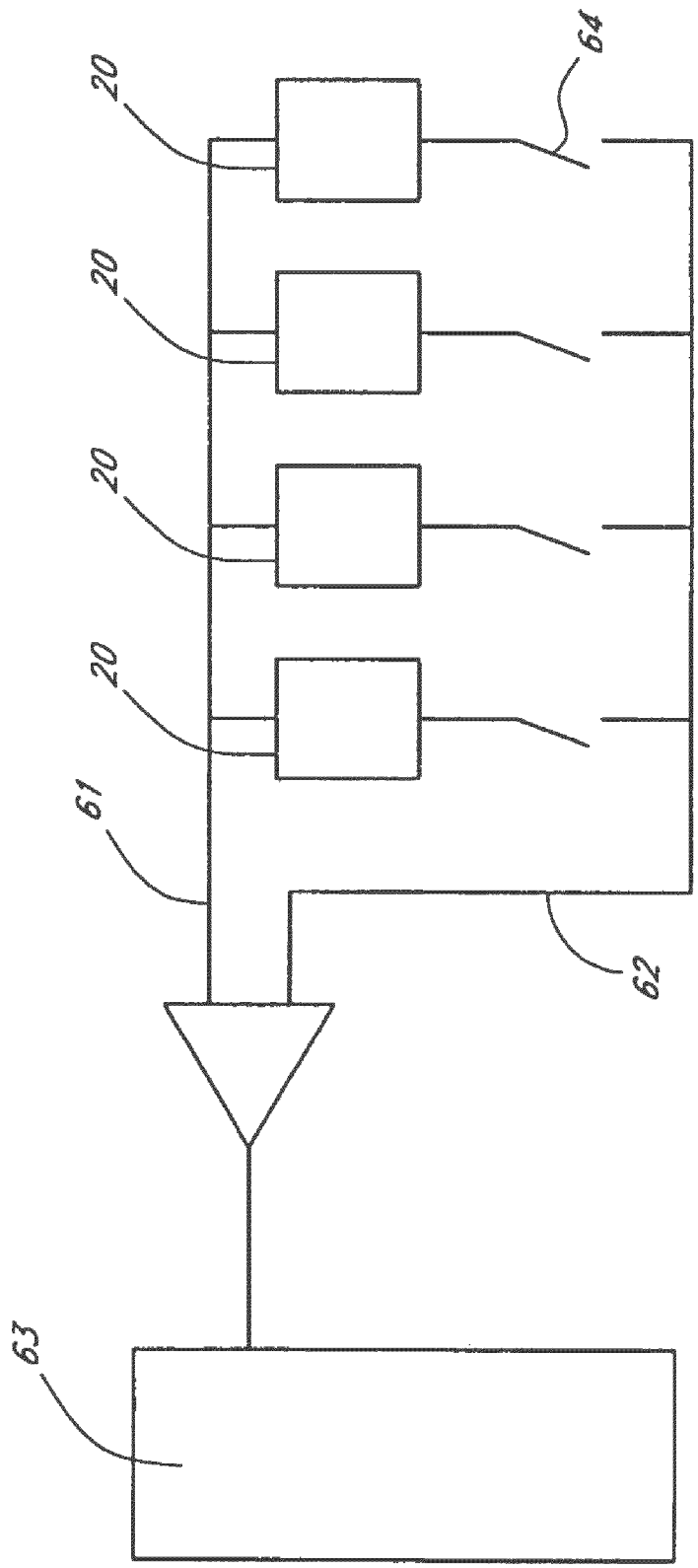
FIG. 9 illustrates a wiring diagram for connecting a plurality of temperature sensors with a common wire.

FIG. 9 illustrates an exemplary embodiment for electrically connecting the temperature sensors 20. In such embodiments, each temperature sensor 20 is coupled to a common wire 61 and is associated with an individual return wire 62. Accordingly, n+1 wires are passed through the tubular body 12 to independently sense the temperature at n temperature sensors 20. The temperature at a selected temperature sensor 20 can be determined by closing a switch 64 to complete a circuit between the return wire 62 associated with the selected thermocouple and the common wire 61. In embodiments wherein the temperature sensors 20 are thermocouples, the temperature can be calculated from the voltage in the circuit using, for example, a sensing circuit 63, which can be located within the external control circuitry 100.

In other embodiments, the temperature sensors 20 can be independently wired. In such embodiments, 2n wires are passed through the tubular body 12 to independently sense the temperature at n temperature sensors 20. In still other embodiments, the flexibility of the tubular body 12 can be improved by using fiber optic based temperature sensors 20. In such embodiments, flexibility can be improved because only n fiber optic members are used to sense the temperature at n independent temperature sensors 20.

Figure 10:
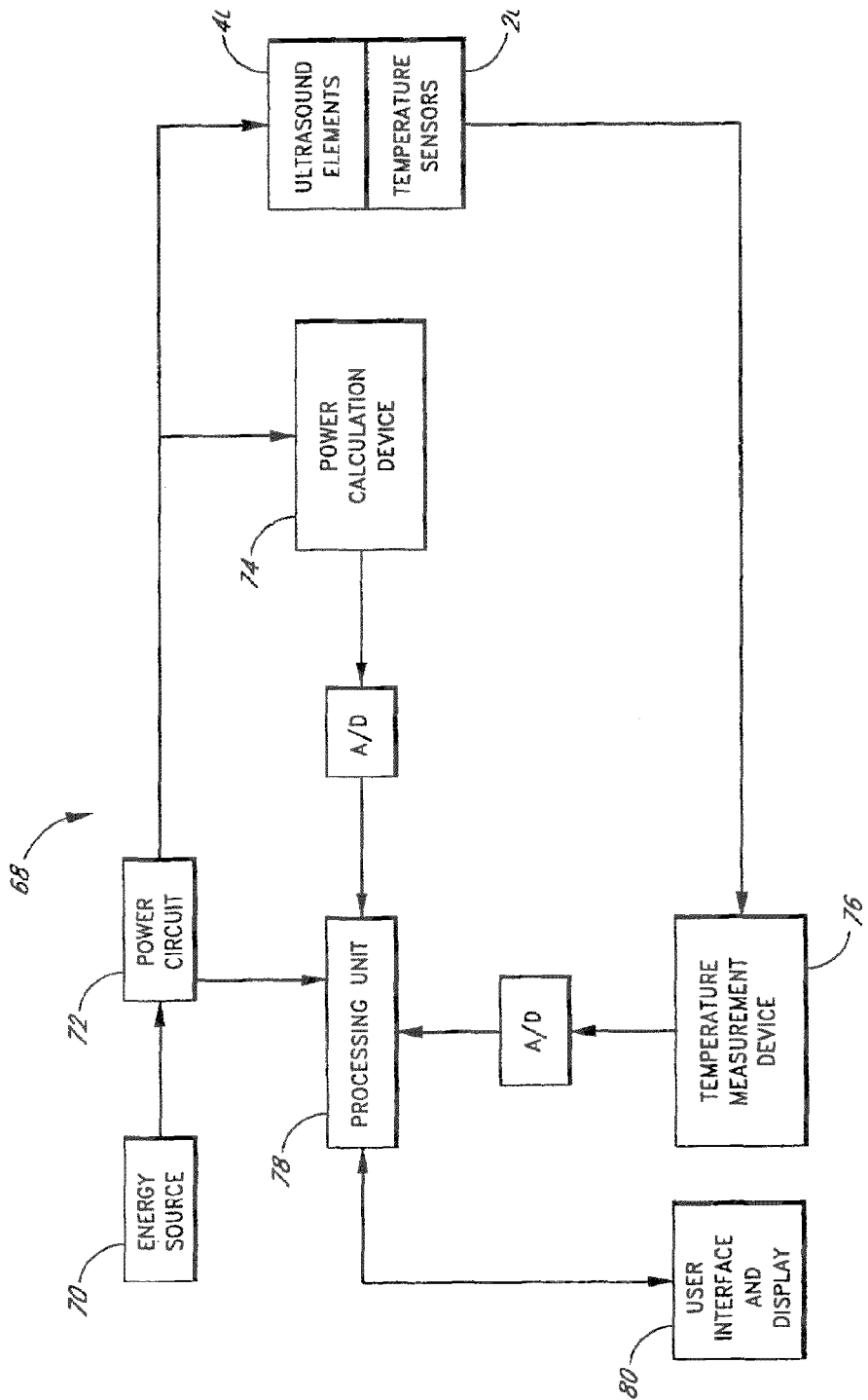
FIG. 10 is a block diagram of a feedback control system for use with an ultrasonic catheter.

FIG. 10 schematically illustrates one embodiment of a feedback control system 68 that can be used with the catheter 10. The feedback control system 68 can be integrated into the control system 100 that is connected to the inner core 34 via cable 45 (as illustrated in FIG. 1). The feedback control system 68 allows the temperature at each temperature sensor 20 to be monitored and allows the output power of the energy source 70 to be adjusted accordingly. A physician can, if desired, override the closed or open loop system.

In an exemplary embodiment, the feedback control system 68 includes an energy source 70, power circuits 72 and a power calculation device 74 that is coupled to the ultrasound radiating members 40. A temperature measurement device 76 is coupled to the temperature sensors 20 in the tubular body 12. A processing unit 78 is coupled to the power calculation device 74, the power circuits 72 and a user interface and display 80.

In an exemplary method of operation, the temperature at each temperature sensor 20 is determined by the temperature measurement device 76. The processing unit 78 receives each determined temperature from the temperature measurement device 76. The determined temperature can then be displayed to the user at the user interface and display 80.

In an exemplary embodiment, the processing unit 78 includes logic for generating a temperature control signal. The temperature control signal is proportional to the difference between the measured temperature and a desired temperature. The desired temperature can be determined by the user (as set at the user interface and display 80) or can be preset within the processing unit 78.

In such embodiments, the temperature control signal is received by the power circuits 72. The power circuits 72 are configured to adjust the power level, voltage, phase and/or current of the electrical energy supplied to the ultrasound radiating members 40 from the energy source 70. For example, when the temperature control signal is above a particular level, the power supplied to a particular group of ultrasound radiating members 40 is reduced in response to that temperature control signal. Similarly, when the temperature control signal is below a particular level, the power supplied to a particular group of ultrasound radiating members 40 is increased in response to that temperature control signal. After each power adjustment, the processing unit 78 monitors the temperature sensors 20 and produces another temperature control signal which is received by the power circuits 72.

In an exemplary embodiment, the processing unit 78 optionally includes safety control logic. The safety control logic detects when the temperature at a temperature sensor 20 exceeds a safety threshold. In this case, the processing unit 78 can be configured to provide a temperature control signal which causes the power circuits 72 to stop the delivery of energy from the energy source 70 to that particular group of ultrasound radiating members 40.

Because, in certain embodiments, the ultrasound radiating members 40 are mobile relative to the temperature sensors 20, it can be unclear which group of ultrasound radiating members 40 should have a power, voltage, phase and/or current level adjustment. Consequently, each group of ultrasound radiating members 40 can be identically adjusted in certain embodiments. For example, in a modified embodiment, the power, voltage, phase, and/or current supplied to each group of ultrasound radiating members 40 is adjusted in response to the temperature sensor 20 which indicates the highest temperature. Making voltage, phase and/or current adjustments in response to the temperature sensed by the temperature sensor 20 indicating the highest temperature can reduce overheating of the treatment site.

The processing unit 78 can also be configured to receive a power signal from the power calculation device 74. The power signal can be used to determine the power being received by each group of ultrasound radiating members 40. The determined power can then be displayed to the user on the user interface and display 80.

As described above, the feedback control system 68 can be configured to maintain tissue adjacent to the energy delivery section 18 below a desired temperature. For example, in certain applications, tissue at the treatment site is to have a temperature increase of less than or equal to approximately 6° C. As described above, the ultrasound radiating members 40 can be electrically connected such that each group of ultrasound radiating members 40 generates an independent output. In certain embodiments, the output from the power circuit maintains a selected energy for each group of ultrasound radiating members 40 for a selected length of time.

The processing unit 78 can comprise a digital or analog controller, such as a computer with software. In embodiments wherein the processing unit 78 is a computer, the computer can include a central processing unit ("CPU") coupled through a system bus. In such embodiments, the user interface and display 80 can include a mouse, a keyboard, a disk drive, a display monitor, a nonvolatile memory system, and/or other computer components. In an exemplary embodiment, program memory and/or data memory is also coupled to the bus.

In another embodiment, in lieu of the series of power adjustments described above, a profile of the power to be delivered to each group of ultrasound radiating members 40 can be incorporated into the processing unit 78, such that a preset amount of ultrasonic energy to be delivered is pre-profiled. In such embodiments, the power delivered to each group of ultrasound radiating members 40 is provided according to the preset profiles.

In an exemplary embodiment, the ultrasound radiating members are operated in a pulsed mode. For example, in one embodiment, the time average acoustic power supplied to each ultrasound radiating member is between about 0.1 watts and about 2 watts. In another embodiment, the time average acoustic power of each ultrasound radiating member is between about 0.3 watts and about 1.5 watts. In yet another embodiment, the time average acoustic power generated by each ultrasound radiating members is approximately 0.45 watts or approximately 1.2 watts. In an exemplary embodiment, the duty cycle is between about 1% and about 50%. In another embodiment, the duty cycle is between about 3% and about 25%. In yet another embodiment, the duty cycles is approximately 7.5% or approximately 15%. In an exemplary embodiment, the pulse averaged acoustic power is between about 0.1 watts and about 20 watts. In another embodiment, the pulse averaged acoustic power per ultrasound radiating member is between approximately 2 watts and approximately 10 watts. In yet another embodiment, the pulse averaged acoustic power per ultrasound radiating member is approximately 2 watts or approximately 5 watts. The amplitude during each pulse can be constant or modulated.

In an exemplary embodiment, the pulse repetition frequency is between about 5 Hz and about 150 Hz. In another embodiment, the pulse repetition rate is between about 10 Hz and about 50 Hz. In yet another embodiment, the pulse repetition frequency is approximately 30 Hz. In an exemplary embodiment, the pulse duration is between about 0.5 millisecond and about 50 milliseconds. In another embodiment, the pulse duration is between about 1 millisecond and about 25 milliseconds. In yet another embodiment, the pulse duration is approximately 2.5 milliseconds or approximately 5 milliseconds.

For example, in one particular embodiment, each ultrasound radiating member is operated at a time average acoustic power of approximately 0.35 watts, a duty cycle of approximately 15%, a pulse repetition rate of approximately 30 Hz, a pulse duration of approximately 5 milliseconds and with a peak rarefactional pressure that can be constant or modulated.

In an exemplary embodiment, the ultrasound radiating member used with the electrical parameters described herein has an acoustic efficiency greater than approximately 50%. In another embodiment, the ultrasound radiating member used with the electrical parameters described herein has an acoustic efficiency greater than approximately 75%. As described herein, the ultrasound radiating members can be formed in a variety of shapes, such as, cylindrical (solid or hollow), flat, bar, triangular, and the like. In an exemplary embodiment, the length of the ultrasound radiating member is between about 0.1 cm and about 0.5 cm, and the thickness or diameter of the ultrasound radiating member is between about 0.02 cm and about 0.2 cm.

Figure 11A:
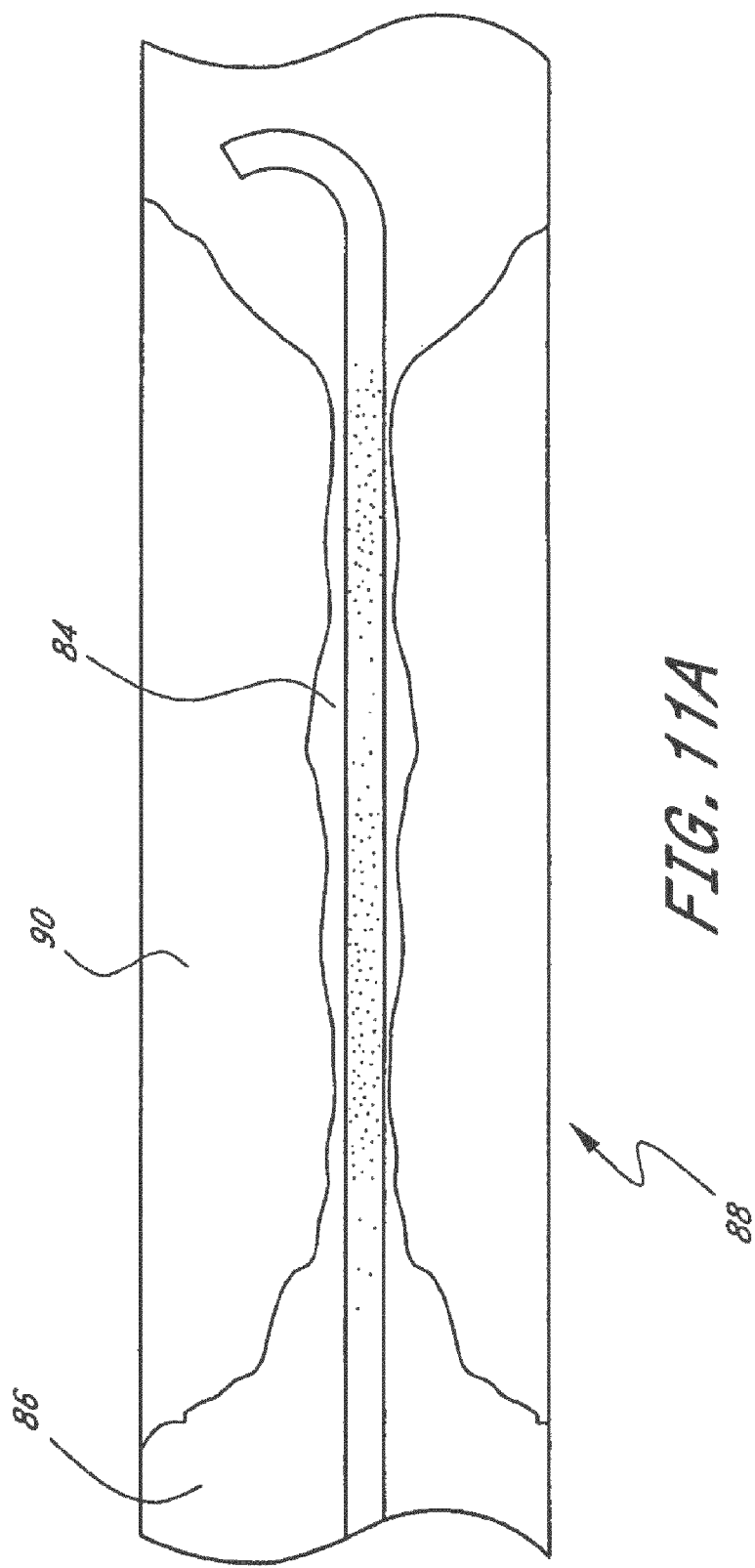
FIG. 11A is a side view of a treatment site.
Figure 11C:
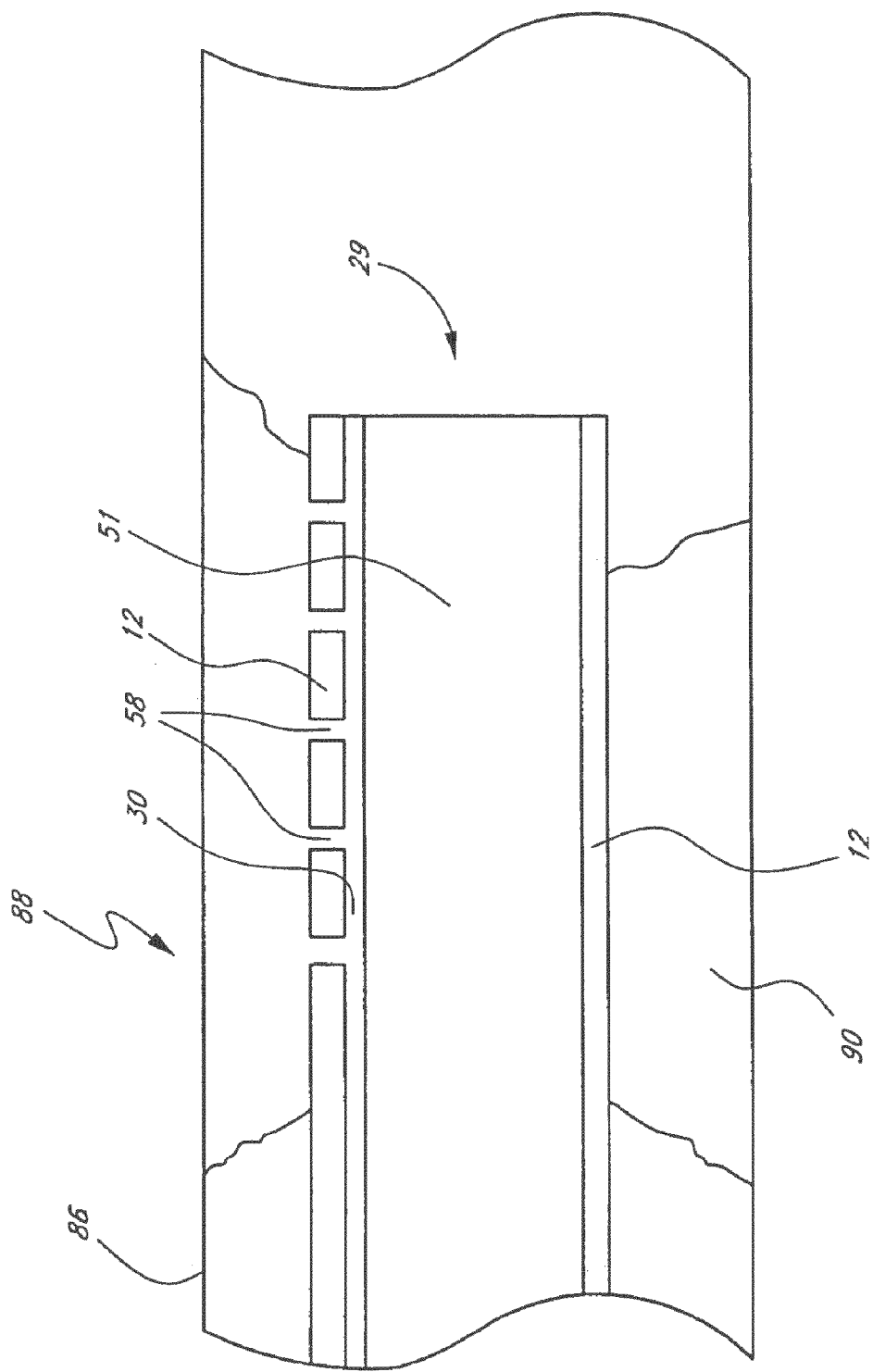
FIG. 11C is a cross-sectional view of the distal end of the ultrasonic catheter of FIG. 11B positioned at the treatment site before a treatment.

FIGS. 11A through 11D illustrate an exemplary method for using certain embodiments of the ultrasonic catheter 10 describe herein. As illustrated in FIG. 11A, a guidewire 84 similar to a guidewire used in typical angioplasty procedures is directed through a patient's vessels 86 to a treatment site 88 that includes a clot 90. The guidewire 84 is optionally directed through the clot 90. Suitable vessels 86 include, but are not limited to, the large periphery blood vessels of the body. Additionally, as mentioned above, the ultrasonic catheter 10 also has utility in various imaging applications or in applications for treating and/or diagnosing other diseases in other body parts.

As illustrated in FIG. 11B, the tubular body 12 is slid over and is advanced along the guidewire 84, for example using conventional over-the-guidewire techniques. The tubular body 12 is advanced until the energy delivery section 18 is positioned at the clot 90. In certain embodiments, radiopaque markers (not shown) are optionally positioned along the tubular body energy delivery section 18 to aid in the positioning of the tubular body 12 within the treatment site 88.

As illustrated in FIG. 10C, after the tubular body 12 is delivered to the treatment site 88, the guidewire 84 is withdrawn from the tubular body 12 by pulling the guidewire 84 from the proximal region 14 of the catheter 10 while holding the tubular body 12 stationary. This leaves the tubular body 12 positioned at the treatment site 88.

As illustrated in FIG. 10D, the inner core 34 is then inserted into the tubular body 12 until the ultrasound assembly 42 is positioned at least partially within the energy delivery section 18. In one embodiment, the ultrasound assembly 42 can be configured to be positioned at least partially within the energy delivery section 18 when the inner core 24 abuts the occlusion device at the distal end of the tubular body 12. Once the inner core 34 is positioned in such that the ultrasound assembly 42 is at least partially within the energy delivery section, the ultrasound assembly 42 is activated to deliver ultrasonic energy to the clot 90. As described above, in one embodiment, ultrasonic energy having a frequency between about 20 kHz and about 20 MHz is delivered to the treatment site.

In an exemplary embodiment, the ultrasound assembly 42 includes sixty ultrasound radiating members 40 spaced over a length of approximately 30 to approximately 50 cm. In such embodiments, the catheter 10 can be used to treat an elongate clot 90 without requiring moving or repositioning the catheter 10 during the treatment. However, in modified embodiments, the inner core 34 can be moved or rotated within the tubular body 12 during the treatment. Such movement can be accomplished by maneuvering the proximal hub 37 of the inner core 34 while holding the backend hub 33 stationary.

Still referring to FIG. 11D, arrows 48 indicate that a cooling fluid can be delivered through the cooling fluid lumen 44 and out the distal exit port 29. Likewise, arrows 49 indicate that a therapeutic compound can be delivered through the fluid delivery lumen 30 and out the fluid delivery ports 58 to the treatment site 88.

The cooling fluid can be delivered before, after, during or intermittently with the delivery of ultrasonic energy. Similarly, the therapeutic compound can be delivered before, after, during or intermittently with the delivery of ultrasonic energy. Consequently, the methods illustrated in FIGS. 11A through 11D can be performed in a variety of different orders than that described above. In an exemplary embodiment, the therapeutic compound and ultrasonic energy are delivered until the clot 90 is partially or entirely dissolved. Once the clot 90 has been sufficiently dissolved, the tubular body 12 and the inner core 34 are withdrawn from the treatment site 88.

Overview of a Small Vessel Ultrasonic Catheter.

Ultrasonic catheters can also be specifically configured to use in the small vessels of a patient's vasculature, such as in the vasculature of a patient's brain. In such a configuration, the catheter is provided with an energy delivery section having increased flexibility, thereby facilitating delivery of the catheter through narrow vessels having small radius turns. FIGS. 12A and 12B are cross-sectional views of the distal region of an exemplary ultrasonic catheter configured for use in the small vasculature.

Similar to the large vessel ultrasonic catheter described herein, an exemplary ultrasonic catheter configured for use in small vessels comprises a multi-component tubular body 202 having a proximal region and a distal region 206. In such embodiments, the catheter tubular body 202 includes an outer sheath 208 that is positioned upon an inner core 210. In one embodiment, the outer sheath 208 comprises extruded Pebax®, PTFE, polyetheretherketone ("PEEK"), PE, polyamides, braided polyamides and/or other similar materials. The outer sheath distal region 206 is adapted for advancement through vessels having a small diameter, such as those in the vasculature of the brain. In an exemplary embodiment, the outer sheath distal region 206 has an outer diameter between about 2 French and about 5 French. In another embodiment, outer sheath distal region 206 has an outer diameter of about 2.8 to 3.2 French. In one exemplary embodiment, the outer sheath 208 has an axial length of approximately 150 centimeters.

In a modified embodiment, the outer sheath 208 comprises a braided tubing formed of, for example, high or low density polyethylenes, urethanes, nylons, and the like. This configuration enhances the flexibility of the tubular body 202. For enhanced maneuverability, especially the ability to be pushed and rotated, the outer sheath 208 can be formed with a variable stiffness from the proximal to the distal end. To achieve this, a stiffening member may be included along the proximal end of the tubular body 202.

The inner core 210 defines, at least in part, a delivery lumen 212, which, in an exemplary embodiment, extends longitudinally along the catheter. The delivery lumen 212 has a distal exit port 214, and is hydraulically connected to a proximal access port (not shown). Similar to the large vessel ultrasonic catheter described herein, the proximal access port can be connected to a source of therapeutic compound or cooling fluid that is to be delivered through the delivery lumen 212.

In an exemplary embodiment, the delivery lumen 212 is configured to receive a guide wire (not shown). In such embodiments, the guidewire has a diameter of between approximately 0.008 and approximately 0.012 inches. In another embodiment, the guidewire has a diameter of about 0.010 inches. In an exemplary embodiment, the inner core 210 comprises polyamide or a similar material which can optionally be braided to increase the flexibility of the tubular body 202.

Still referring to FIGS. 12A and 12B, the tubular body distal region 206 includes an ultrasound radiating member 224. In such embodiments, the ultrasound radiating member 224 comprises an ultrasound transducer, which converts, for example, electrical energy into ultrasonic energy. In a modified embodiment, the ultrasonic energy can be generated by an ultrasound transducer that is remote from the ultrasound radiating member 224 and the ultrasonic energy can be transmitted via, for example, a wire to the ultrasound radiating member 224.

In the illustrated embodiment, the ultrasound radiating member 224 is configured as a hollow cylinder. As such, the inner core 210 extends through the lumen of the ultrasound radiating member 224. The ultrasound radiating member 224 is secured to the inner core 210 in a suitable manner, such as using an adhesive. A potting material can also be used to further secure the ultrasound radiating member 224 to the inner core 210.

In other embodiments, the ultrasound radiating member 224 can have a different shape. For example, the ultrasound radiating member 224 can take the form of a solid rod, a disk, a solid rectangle or a thin block. In still other embodiments, the ultrasound radiating member 224 can comprise a plurality of smaller ultrasound radiating members. The illustrated configuration advantageously provides enhanced cooling of the ultrasound radiating member 224. For example, in one embodiment, a therapeutic compound can be delivered through the delivery lumen 212. As the therapeutic compound passes through the lumen of the ultrasound radiating member 224, the therapeutic compound can advantageously remove excess heat generated by the ultrasound radiating member 224. In another embodiment, a fluid return path can be formed in the region 238 between the outer sheath 208 and the inner core 21 such that coolant from a coolant system can be directed through the region 238.

In an exemplary embodiment, the ultrasound radiating member 224 produces ultrasonic energy having a frequency of between about 20 kHz and about 20 MHz. In one embodiment, the frequency of the ultrasonic energy is between about 500 kHz and about 20 MHz, and in another embodiment the frequency of the ultrasonic energy is between about 1 MHz and about 3 MHz. In yet another embodiment, the ultrasonic energy has a frequency of about 1.7 MHz.

In the illustrated embodiment, ultrasonic energy is generated from electrical input power supplied to the ultrasound radiating member 224 through a wires 226, 228 that extend through the catheter body 202. The wires 226, 228 can be secured to the inner core 210, lay along the inner core 210 and/or extend freely in the region 238 between the inner core 210 and the outer sheath 208. In the illustrated configuration, the first wire 226 is connected to the hollow center of the ultrasound radiating member 224, while the second wire 228 is connected to the outer periphery of the ultrasound radiating member 224. In such embodiments, the ultrasound radiating member 224 comprises a transducer formed of a piezoelectric ceramic oscillator or a similar material.

Still referring to the exemplary embodiment illustrated in FIGS. 12A and 12B, the catheter further includes a sleeve 230 that is generally positioned about the ultrasound radiating member 224. The sleeve 230 is comprises a material that readily transmits ultrasonic energy. Suitable materials for the sleeve 230 include, but are not limited to, polyolefins, polyimides, polyester and other materials having a relatively low absorbance of ultrasonic energy. The proximal end of the sleeve 230 can be attached to the outer sheath 208 with an adhesive 232. To improve the bonding of the adhesive 232 to the outer sheath 208, a shoulder 227 or notch can be formed in the outer sheath 208 for attachment of the adhesive 232 thereto. In an exemplary embodiment, the outer sheath 208 and the sleeve 230 have substantially the same outer diameter.

In a similar manner, the distal end of the sleeve 230 can be attached to a tip 234. As illustrated, the tip 234 is also attached to the distal end of the inner core 210. In an exemplary embodiment, the tip 234 is between about 0.5 mm and about 4.0 mm long. In another embodiment, the tip is about 2.0 mm long. In the illustrated exemplary embodiment, the tip 234 is rounded in shape to reduce trauma or damage to tissue along the inner wall of a blood vessel or other body structure during advancement of the catheter to a treatment site.

Referring now to the exemplary embodiment illustrated in FIG. 12B, the catheter includes at least one temperature sensor 236 in the tubular body distal region 206. The temperature sensor 236 can be positioned on or near the ultrasound radiating member 224. Suitable temperature sensors include but are not limited to, diodes, thermistors, thermocouples, RTDs and fiber optic temperature sensors that used thermalchromic liquid crystals. In an exemplary embodiment, the temperature sensor 236 is operatively connected to a control system via a control wire that extends through the tubular body 202. As described above for the large vessel ultrasonic catheter, the control box includes a feedback control system having the ability to monitor and control the power, voltage, current and phase supplied to the ultrasound radiating member 224. Thus, the temperature along the relevant region of the catheter can be monitored and controlled for optimal performance. Details of the control box can also be found in U.S. patent application Ser. No. 10/309,388, filed 3 Dec. 2002, now U.S. Pat. No. 7,220,239 the entire disclosure of which is hereby incorporated herein by reference.

The small vessel ultrasound catheters disclosed herein can be used to remove an occlusion from a small blood vessel. In an exemplary method of use, a guidewire is percutaneously inserted into the patient's vasculature at a suitable insertion site. The guidewire is advanced through the vasculature toward a treatment site where the vessel is wholly or partially occluded. The guidewire is then directed at least partially through the thrombus.

After advancing the guidewire to the treatment site, the catheter is then inserted into the vasculature through the insertion site, and advanced along the guidewire towards the treatment site using, for example, over-the-guidewire techniques. The catheter is advanced until the tubular body distal region 206 is positioned near or in the occlusion. The tubular body distal region 206 optionally includes one or more radiopaque markers to aid in positioning the catheter at the treatment site.

After placing the catheter at the treatment site, the guidewire can then be withdrawn from the delivery lumen 212. A source of therapeutic compound, such as a syringe with a Luer fitting, can then be attached to the proximal access port. This allows the therapeutic compound to be delivered through the delivery lumen 212 and the distal exit port 214 to the occlusion.

The ultrasound radiating member 224 can then be activated to generate ultrasonic energy. As described above, in an exemplary embodiment, the ultrasonic energy has a frequency between about 20 kHz and about 20 MHz. In one embodiment, the frequency of the ultrasonic energy is between about 500 kHz and about 20 MHz, and in another embodiment the frequency of the ultrasonic energy is between about 1 MHz and about 3 MHz. In yet another embodiment, the ultrasonic energy has a frequency of about 1.7 MHz. The therapeutic compound and ultrasound energy can be applied until the occlusion is partially or entirely dissolved. Once the occlusion has been sufficiently dissolved, the catheter can be withdrawn from the treatment site.

Further information on exemplary methods of use, as well as on modified small vessel catheter constructions, are available in U.S. patent application Ser. No. 10/309,417, filed 3 Dec. 2002, the entire disclosure of which is hereby incorporated herein by reference.

Treatment of Vascular Occlusions Using Ultrasonic Energy and Microbubble-Therapeutic Compound.

In certain embodiments, the therapeutic compound delivered to the treatment site includes a plurality of microbubbles having, for example, a gas formed therein. A combined microbubbles and therapeutic compound is referred to herein as a "microbubble-therapeutic compound". In some embodiments, the microbubbles are formed by entrapping micro spheres of gas into the therapeutic compound. In some embodiments, this is accomplished by agitating the therapeutic compound while blowing a gas into the therapeutic compound. In other embodiments, this is accomplished by exposing the therapeutic compound to ultrasonic energy with a sonicator under a gaseous atmosphere while vibrating the therapeutic compound. Other techniques can be used in other embodiments. Exemplary gases that are usable to form the microbubbles include, but are not limited to, air, oxygen, carbon dioxide, and inert gases. In some embodiments, the microbubble-therapeutic compound can include approximately $4 \times 10^7$ microbubbles per milliliter of liquid. In some embodiments, the microbubble-therapeutic compound can include approximately $6.5 \times 10^6$ microbubbles per milliliter of liquid. In some embodiments, the microbubble-therapeutic compound can include between approximately $4 \times 10^6$ and approximately $4 \times 10^8$ microbubbles per milliliter of liquid. In some embodiments, the microbubble-therapeutic compound can include approximately $2 \times 10^8$ to approximately $8 \times 10^8$ microbubbles per milliliter of liquid, approximately $2 \times 10^8$ to approximately $5 \times 10^8$ microbubbles per milliliter of liquid, or approximately $5 \times 10^8$ to approximately $8 \times 10^8$ microbubbles per milliliter of liquid. In some embodiments the microbubbles in the microbubble-therapeutic compound have a diameter of between approximately 0.1 μm and approximately 30 μm. In some embodiments, the microbubbles have a diameter of about 0.1 to about 10 μm, about 0.2 to about 10 μm, about 0.5 to about 10 μm, about 0.5 to about 5 μm, or about 0.5 μm. In some embodiments, the microbubbles have a diameter of less than or equal to approximately 10 μm, approximately 5 μm, or approximately 2.5 μm. Other parameters can be used in other embodiments.

In some embodiments, the efficacy of the therapeutic compound is enhanced by the presence of the microbubbles contained therein. In some embodiments, the microbubbles can act as a nucleus for cavitation, and thus allow cavitation to be induced at lower levels of peak rarefaction acoustic pressure. Therefore, a reduced amount of peak rarefaction acoustic pressure can be delivered to the treatment site without reducing the efficacy of the treatment. Reducing the amount of ultrasonic pressure delivered to the treatment site reduces risks associated with overheating the treatment site, and, in certain embodiments, also reduces the time required to treat a vascular occlusion. In some embodiments, cavitation also promotes more effective diffusion and penetration of the therapeutic compound into surrounding tissues, such as the vessel wall and/or the clot material. Furthermore, in some embodiments, the mechanical agitation caused motion of the microbubbles is effective in mechanically breaking up clot material.

Table 1 summarizes the results of percent clot lysis when the clot was treated with rt-PA at different concentrations without ultrasound, with ultrasound and with both ultrasound and microbubbles.

TABLE 1

Percent clot lysis (AVG ± SD) for each treatment group.

| Rt-PA conc. (mg/ml) | Clot treated with Rt-PA (%) | Clot treated with Rt-PA at 1.3 MPa (%) | Clot treated with Rt-PA at 2.1 MPa (%) | Clot treated with Rt-PA + microbubbles at 1.3 MPa (%) | Clot treated with Rt-PA + microbubbles at 2.1 MPa (%) |
|---|---|---|---|---|---|
| 0.009 | 3.1 ± 2.6 | 12.1 ± 2.0 | 16.0 ± 2.6 | 23.9 ± 2.2 | 27.7 ± 1.4 |
| 0.05 | 9.7 ± 2.1 | 24.8 ± 3.2 | 33.1 ± 3.0 | 40.5 ± 4.9 | 48.3 ± 6.3 |
| 0.3 | 16.4 ± 2.9 | 30.4 ± 2.4 | 41.8 ± 2.9 | 44.9 ± 2.6 | 60.6 ± 2.1 |
| 0.5 | 17.7 ± 3.4 | 31.5 ± 2.5 | 54.0 ± 4.2 | 46.7 ± 2.9 | 64.7 ± 3.9 |

In some embodiments, the lysis rate of the clot can be increased by increasing the concentration of the dissolution compound (i.e. therapeutic compound) in the microbubble-therapeutic compound. In some embodiments, increasing the dissolution compound concentration of rt-PA from approximately 0.009 to approximately 0.05 mg/mL can increase the lysis rate of the clot approximately 3 times. For example, as shown in Table 1 above, the percent clot lysis can be increased from approximately 3.1±2.6% to approximately 9.7±2.1%. In some embodiments, increasing the concentration of the dissolution compound can yield a positive trend toward increased lysis rate. For example, the percent clot lysis achieved with approximately 0.3 mg/mL and approximately 0.5 mg/mL of dissolution compound concentration can be approximately 16.4±2.9% and approximately 17.7±3.4%, respectively.

The employment of ultrasonic energy to dissolution compounds in conjunction with microbubbles can significantly enhance clot lysis compared to only using the dissolution compounds, as shown in Table 1 above. Application of ultrasonic pressure at approximately 1.3 MPa with microbubble-therapeutic compound augmented dissolution compound mediated thrombolysis by approximately 3.9, 2.6, 1.9 and 1.8 times at rt-PA concentrations of approximately 0.009, 0.05, 0.3, and 0.5 mg/mL, respectively. With respect to the same rt-PA concentrations, using ultrasonic energy at approximately 2.1 MPa enhanced thrombolysis by approximately 5.1, 3.4, 2.6, and 3.1 times.

In an exemplary embodiment, a therapeutic compound combined with microbubbles (i.e., microbubble-therapeutic compound) is delivered using the various embodiments of the ultrasonic catheters disclosed herein. However, in certain embodiments, modifications to the catheter design, and/or to the method of use, are implemented to improve the efficacy of a microbubble-based vascular occlusion treatment. In particular, these modifications are intended to reduce the destruction of microbubbles within the ultrasonic catheter. For example, the microbubbles occasionally burst when exposed to ultrasonic energy, regardless of whether that exposure occurs inside or outside the fluid delivery lumens of the ultrasonic catheter. Therefore, these modifications are intended to reduce the exposure of the microbubble-therapeutic compound to ultrasonic energy before the microbubble-therapeutic compound is expelled from the catheter and is delivered to the treatment site.

In one embodiment, a microbubble-therapeutic compound is infused intra-arterially or intravenously to the treatment site before the ultrasound radiating members are activated. Therefore, once the ultrasound radiating members begin to generate ultrasonic energy, the microbubble-therapeutic compound is already at the treatment site. In such embodiments, the microbubble-therapeutic compound is delivered using the same catheter that is used to deliver the ultrasonic energy. In a modified embodiment, the microbubble-therapeutic compound is delivered using a different catheter than that used to deliver the ultrasonic energy, and delivery of the microbubble-therapeutic compound to the treatment site is optionally via the general vascular circulation.

In an embodiment that is particularly advantageous for use with an ultrasonic catheter having a cylindrical ultrasound radiating member, such as illustrated in FIGS. 12A and 12B, an insulating chamber is used to reduce the amount of ultrasonic energy that is delivered into the catheter fluid delivery lumen. Specifically, an insulating chamber is positioned between the ultrasound radiating member and the delivery lumen. In such embodiments, the insulating chamber is filled with a material that does not efficiently transmit ultrasonic energy, thereby reducing the amount of ultrasonic energy reaching the fluid delivery lumen. Exemplary materials that can be put into the insulating chamber include, but are not limited to, air, nitrogen and oxygen. In a modified embodiment, an evacuated chamber is used.

Figure 13:
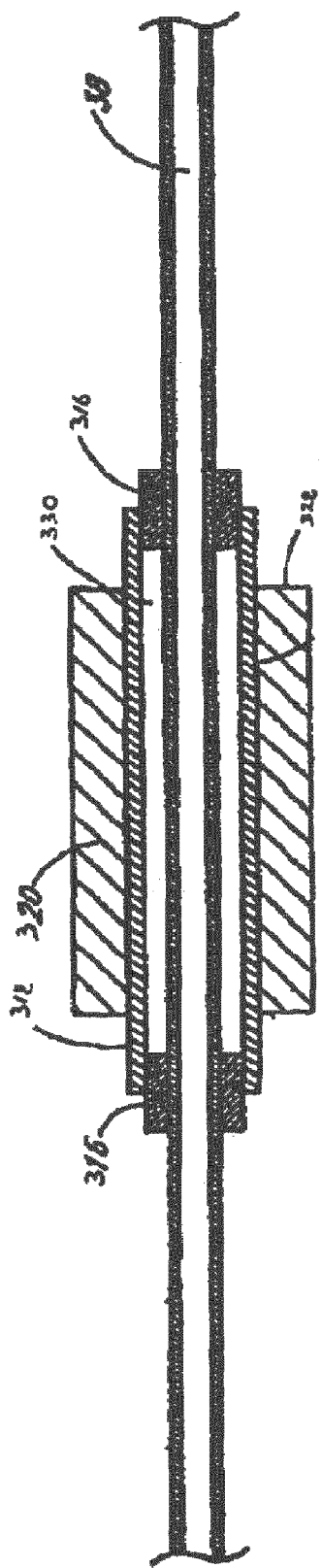
FIG. 13 is a cross-sectional view of an ultrasound radiating member separated from a delivery lumen by a chamber.

FIG. 13 illustrates an exemplary embodiment of an ultrasound catheter having an ultrasound radiating member 320 separated from a delivery lumen 338 by an insulating chamber 330. The ultrasound radiating member 320 is offset from the delivery lumen 338 using spacers 316 and support members 318. Other configurations can be used in other embodiments. Additional information on using chambers to spatially direct ultrasonic energy can be found in U.S. Pat. Nos. 6,582,392 and 6,676,626, the entire disclosure of which is incorporated herein by reference.

Figure 14:
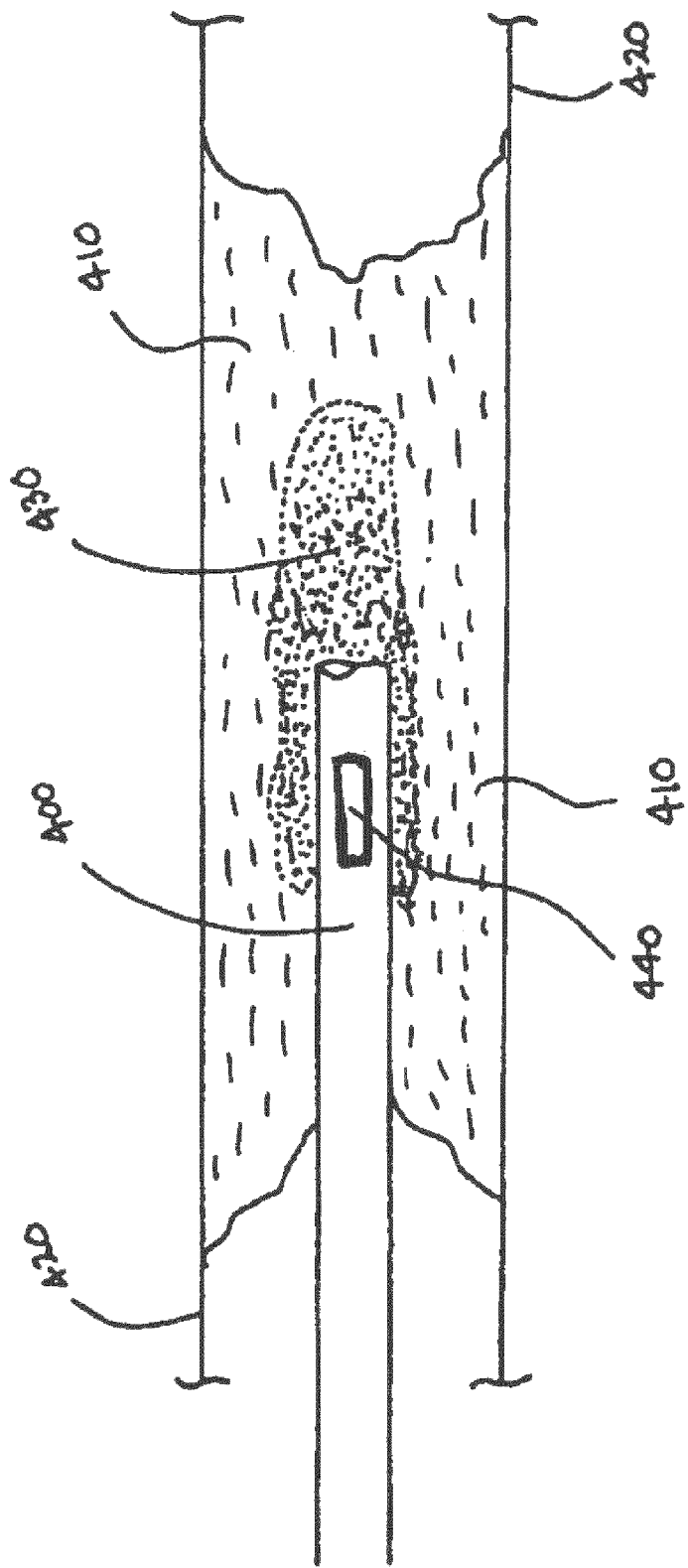
FIG. 14 is a cross-sectional view of an exemplary technique for applying ultrasonic energy to an infused microbubble-therapeutic compound.

In one embodiment, the microbubble-therapeutic compound is injected directly into a vascular obstruction—such as a clot—at the treatment site. A schematic illustration of this embodiment is provided in FIG. 14. Specifically, FIG. 14 illustrates a catheter 400 positioned within an occlusion 410 at a treatment site within a patient's vasculature 420. A microbubble-therapeutic compound 430 has been infused into the occlusion 410 from the catheter 400. Once the microbubble-therapeutic compound has been sufficiently infused, one or more ultrasound radiating members 440 mounted within the catheter 400 can be energized, thereby delivering ultrasonic energy to the infused microbubble-therapeutic compound 430. The catheter 400 is optionally repositioned to direct additional ultrasonic energy into the infused microbubble-therapeutic compound 430. This technique allows microbubbles to be suspended within the obstruction. In such embodiments, ultrasonic energy is applied to the obstruction, thereby causing mechanical agitation of the microbubbles. The mechanical agitation of the microbubbles is effective in mechanically breaking up clot material.

Microbubble Concentrations

In some embodiments, a percentage of the microbubbles in the infusion liquid can be reduced when ultrasonic energy is introduced. Experimental results show that the percent retention of Albumin-shelled Octafluoropropane-filled microbubbles delivered at approximately 6, 12, and 18 ml/h flow rates in the absence of ultrasonic energy were approximately 5.9, 5.4, and 8.9%, and in the presence of ultrasonic energy at a peak rarefaction acoustic pressure of approximately 1.3 MPa, were approximately 1.5, 0.8, and 0.12%, respectively. Similarly, the percent retention of lipid-shelled Sulfurhexafluoride-filled microbubbles delivered at approximately 6, 12, and 18 ml/h flow rates in the absence of ultrasonic energy were approximately 3.5, 6.4, and 14%, and in the presence of ultrasonic energy at a peak rarefaction acoustic pressure of approximately 1.3 MPa, were approximately 0.7, 1, and 0.5%, respectively.

In some embodiments, upon delivery of microbubbles through the catheter, there can be a significant shift towards smaller diameter microbubbles. Some causes of this phenomenon can include possible pressure-dependent compression, disruption, and/or shrinkage of the microbubbles due to acceleration of the rate of gas diffusion from the microbubbles in response to pressure-induced shifts in the ambient medium. In some embodiments, when the microbubble-therapeutic compound passes through the catheter lumen while exposed to the inward ultrasound field of the cylindrical transducer, additional mechanisms such as cavitation and rectified diffusion can further affect microbubble physical properties.

In some embodiments, the microbubble-therapeutic compound concentrations can be diluted prior to delivery to the ultrasound catheter for optimal efficacy. Experimental results show that the clot lysis can reach an optimal peak when the microbubble-therapeutic compound concentrations are approximately 1:100 v/v dilution. For example, in the absence of dissolution compounds, Albumin-shelled Octafluoropropane-filled microbubble concentrations diluted to approximately 1:10, 1:100, and 1:200 by volume exposed to ultrasonic energy at approximately 2.1 MPa for 10 minutes resulted in a percent clot lysis of 12.6±2.4%, 13.9±1.6%, and 7.2±2.5%, respectively. In the presence of dissolution compounds (e.g., rt-PA) of approximately 0.05 mg/mL, clots exposed to ultrasonic energy at approximately 1.3 MPa demonstrated a clot lysis of 22.5±2.4%, 43.2±2.4%, and 27.2±2.1% for administered microbubble-therapeutic compound concentrations diluted to approximately 1:10, 1:100, and 1:200 by volume, respectively. With respect to the same microbubble-therapeutic compound concentrations, the clots exposed to ultrasonic energy at approximately 2.1 MPa showed slightly higher clot lysis of 27.6±2.6%, 45.7±3.0% and 30.7±1.3%. The microbubble-therapeutic compound was administered to the clot at flow rates of 6, 12, and 18 mL/h.

As evidenced in the experimental results, the infusion of microbubble-therapeutic compound into the acoustic field propagating the clot can cause an acoustic impedance mismatch in the ultrasound pathway. The interface of shell and gas of each bubble can act as strong scatterer of the incident sound field and can extend the length over which ultrasound penetrate the tissue. This can be one of the responsible mechanisms for enhanced clot lysis, however, if bubble concentration contained within a volume of clot is too high they can effectively trap the incident acoustic energy within that region and can prevent further interaction of the acoustic energy with the clot during thrombolysis. Thus, the microbubble-therapeutic compound having an "original microbubble concentration" may be diluted prior to delivery to the ultrasound catheter for infusion. The diluted microbubble-therapeutic compound has an "initial microbubble concentration" when it is delivered to the ultrasound catheter.

In some embodiments, the lower lysis rate for a microbubble-therapeutic compound dilution factor of approximately 1:10 by volume can be explained as a partial acoustic shielding due to relatively high bubble concentrations. Conversely, the reduced clot lysis at microbubble-therapeutic compound concentrations of approximately 1:200 by volume is shown to be lower than the required concentration to reach maximum bioeffect. The experimental data suggests that at approximately 1:10 dilution, microbubble-therapeutic compounds can cause a shielding effect preventing ultrasound to effectively reach beyond the bubble cloud, and at approximately 1:200 dilution the microbubble-therapeutic compound concentration is lower than optimal.

Thus, in some embodiments, the microbubble-therapeutic compound is first diluted to between about 10% and about 0.5% by volume, between about 5% and about 0.5% by volume, between about 2% and about 0.5% by volume, or between about 1% and about 0.5% by volume of the original microbubble concentration when delivered to the catheter. In some embodiments, the microbubble-therapeutic compound is diluted to less than or equal to approximately 1% by volume when delivered to the catheter. The microbubble concentration in the diluted microbubble-therapeutic compound at the deliverance of the microbubble-therapeutic compound to the catheter is designated the "initial microbubble concentration."

In the presence of rt-PA concentrations of approximately 0.05 and 0.5 mg/mL, lipid-shelled Sulfurhexafluoride-filled microbubble-therapeutic compounds diluted to 1:100 were administered to a clot. Clots exposed to ultrasonic energy at an acoustic pressure of approximately 1.3 MPa and 2.1 MPa demonstrated a clot lysis of 36.1±2.6% and 53.1±2.6%, respectively, at a rt-PA concentration of 0.05 mg/mL, and 37.5±2.6% and 62.6±5.7%, respectively, at a rt-PA concentration of 0.5 mg/mL. The microbubble-therapeutic compound was administered to the clot at flow rates of 6, 12, and 18 mL/h.

In some embodiments, intra-arterial treatment can involve application of microbubble-therapeutic compounds and ultrasound to the interior of the clot concurrently. Intra-arterial treatment can be applied up to 8 hours after symptoms onset, and the required therapeutic compound for a 2-hour treatment can include approximately <1% concentration of microbubble-therapeutic compounds. The intra-clot delivery of a low concentration of microbubble-therapeutic compounds can significantly reduce the occurrence of cardiopulmonary reactions of patients to these agents and make this application very cost effective.

In a study, a maximum clot lysis rate using the dissolution compound rt-PA was achieved by using a concentration of 0.5 mg/mL. Application of ultrasonic energy of 1.7 MHz frequency with a calculated acoustic peak rarefaction pressures of about 1.3 MPa and about 2.1 MPa increased the rt-PA induced lysis rate at 0.5 mg/L by 1.8 and 3.1 times, respectively.

In some embodiments, high-frequency (e.g., >1 MHz), low-pressure ultrasonic energy (e.g., ≤5.2 MPa) can enhance thrombolysis via absorption of ultrasound energy by clot components, unrelated to thermal and cavitational effects. In the absence of cavitation, it can be the absorption of ultrasound energy by blood clot components that has the greatest potential for inducing bioeffects. In some embodiments, the noncavitational ultrasound phenomena reported to enhance rt-PA thrombolysis, increase porosity of the clot and enhance fluid streaming within the clot, can be attributed to ultrasound absorption.

In some embodiments, due to geometrical spreading, the acoustic pressure generated by an acoustic transducer drops exponentially with the distance from the transducer surface. Some studies have shown that the effectiveness of ultrasonic energy enhanced thrombolysis can be dependent on acoustic pressure generated by transducer. Therefore, ultrasound efficiency in enhancing enzymatic thrombolysis can decrease with distance from the transducer. Thus, there can be a limited volume of the clot treated with effective ultrasound pressures for thrombolysis. In some embodiments, the magnitude of the acoustic pressure on the acoustic source surface is proportionate to the clot volume that can be treated with ultrasonic device.

In relatively low acoustic rarefaction pressure amplitudes, a bubble can experience prolonged linear or nonlinear oscillation about its equilibrium radius in what is called a stable cavitation. In some embodiments, the bubble can experience a violent collapse followed by an unstable expansion of the bubble radius in what is called inertial cavitation. In some embodiments, it is unlikely that stable cavitation will cause mechanical disruption of the clot. The violent collapse of an inertial bubble, however, can release a significant amount of energy in the form of an acoustic shock wave that could potentiate clot fragmentation.

In some embodiments, the stable cavitation and inertial cavitation phenomena can explain clot lysis efficacy at different acoustic pressures of ultrasonic energy when applied in combination with microbubble-therapeutic compounds and in the absence of dissolution compounds. Experimental data shows a lack of detectable clot weight reduction with ultrasonic energy at a peak rarefaction acoustic pressure of approximately 1.3 MPa, which can indicate that stable cavitation may be the dominant cavitation mechanism at this acoustic pressure. However, the statistically significant clot weight reduction achieved with ultrasonic energy at a peak rarefaction acoustic pressure of approximately 2.1 MPa may suggest that the peak rarefaction pressure threshold for inertial cavitation of microbubbles can be higher than 1.3 MPa and lower or equal to 2.1 MPa. In other embodiments, the ultrasound energy having a peak rarefaction acoustic pressure less or equal to: approximate 5.0 MPa, approximately 3 MPa, approximately 2.5 MPa, or approximately 2.1 MPa may also be used.

In some embodiments, microbubbles that undergo stable cavitation can have the potential to scatter and extend the propagation path of ultrasound. The microbubbles can convert the acoustic energy to mechanical energy by means of bubble dynamics and can cause fluid microstreaming on their boundary with the clot. The oscillating microbubbles can act as small microscopic pumps that promote local mass transfer and can facilitate deeper penetration of dissolution compounds into the clot matrix. This can explain the further increased clot lysis rate from approximately 1.8 to 2.6 times when 1:100 diluted microbubble-therapeutic compounds were added to an ultrasonic energy at a peak rarefaction acoustic pressure of approximately 1.3 MPa, and from 3.1 to 3.7 times when 1:100 diluted microbubble-therapeutic compounds were added to an ultrasonic energy at a peak rarefaction acoustic pressure of approximately 2.1 M. For this data, the clot was in the presence of dissolution compounds of 0.5 mg/mL.

The presence of microbubbles in the immediate surrounding of a catheter tip mounted ultrasound transducer can introduce acoustic mismatch interfaces, which can change the load characteristics of the transducer. In some situations, this can result in an electrical impedance shift, decreased efficiency and increased temperatures of the transducer. However, low power impedance measurements of the catheter mounted transducers in the presence of microbubble-therapeutic compounds (diluted 1:100 v/v) shows that seeded plasma clots can be similar to plain plasma clots. Considering that microbubble-therapeutic compounds diluted 1:100 v/v represents the initial microbubble concentration prior to the catheter delivery, upon delivery through the catheter into the clot, this microbubble concentration is likely reduced to less than 1% of the initial concentration in the presence of ultrasound transmission.

In other words, after the microbubble-therapeutic compound passes through the distal tip of the catheter that is not acoustically isolated, the effective microbubble concentration of the microbubble-therapeutic compound at the point of delivery to the vascular occlusion is about 1% by volume of the initial microbubble concentration when the microbubble-therapeutic compound is delivered to the catheter. Accordingly, the effective or final microbubble concentration in the microbubble-therapeutic compound when delivered to the occlusion or the clot in the presence of the ultrasound transmission is between about 0.1% and about 0.005% by volume, between about 0.05% and about 0.005% by volume, between about 0.02% and about 0.005% by volume, or between about 0.01% and about 0.005% by volume of the original microbubble concentration prior to the dilution. In some embodiments, the effective microbubble concentration in the microbubble-therapeutic compound is less than or equal to approximately 0.01% by volume of the original microbubble concentration at deliverance into the occlusion or the clot.

Thus, it can be inferred that the final microbubble concentration in the clot does not have an unloading effect on the transducer. The fact that continuous monitored surface temperature of the transducers showed no temperature increase for the microbubble treatment groups as compared to other groups can be seen as further evidence of the unloading effect of low microbubble concentrations on catheter mounted transducers.

In some embodiments, the effective concentration of microbubbles delivered at the tip of the powered on catheter into the clot is about 5,000 to about 10,000 microbubbles (MB)/mL. In some embodiments, the effective concentration of microbubbles is about 5,000 to about 8,500 MB/mL, about 5,000 to about 7,000 MB/mL, about 6,500 to about 10,000 MB/mL, or about 8,000 to about 10,000 MB/mL. In some embodiments, the disclosed ranges of the effective concentration of microbubbles can enhance the sonothrombolysis.

The results disclosed above demonstrates the safety and efficacy of using ultrasonic energy at a peak rarefaction acoustic pressure of approximately 1.3 MPa in enhancing dissolution compound mediated clot lysis in an intra-arterial approach has been demonstrated in clinical trials. In addition, using microbubbles in neurovasculature of stroke patients to accelerate thrombolysis using ultrasound was not associated with any increased risk as compared to standard treatments. Hence, intra-arterial therapy consisting of intra-clot delivery of ultrasound, dissolution compounds, and microbubble-therapeutic compounds (diluted 1:100) can be safely applied and evaluated in ischemic stroke patients.

In some embodiments, the use of ultrasonic energy at a peak rarefaction acoustic pressure of approximately 2.1 MPa can demonstrate better potency in increasing the dissolution compound mediated clot lysis rate in the presence and/or absence of microbubbles.

As disclosed herein, intra-arterial application of dissolution compounds and low dose of microbubbles in the presence of ultrasonic energy can be considered as a viable treatment for treatment of vascular occlusions.

SCOPE OF THE INVENTION

While the foregoing detailed description discloses several embodiments of the present invention, it should be understood that this disclosure is illustrative only and is not limiting of the present invention. It should be appreciated that the specific configurations and operations disclosed can differ from those described above, and that the methods described herein can be used in contexts other than treatment of vascular occlusions.

We claim:

1. A method of treating a vascular occlusion located at a treatment site within a patient's vasculature, the method comprising:
    positioning an ultrasound assembly at the treatment site;
    delivering a diluted microbubble-therapeutic compound from the ultrasound assembly to the vascular occlusion, wherein the diluted microbubble-therapeutic compound has:
        (1) an initial microbubble concentration of between 500,000-1,000,000 microbubble/mL; or
        (2) an effective microbubble concentration of between 5,000-10,000 microbubble/mL; and
    delivering ultrasonic energy from the ultrasound assembly to the vascular occlusion concurrently.

2. The method of claim 1, wherein the dilute microbubble-therapeutic compound comprises biological or synthetic-shelled microbubbles.

3. The method of claim 2, wherein the biological or synthetic-shelled microbubbles are less than or equal to approximately 10 micrometers in diameter.

4. The method of claim 1, wherein the diluted microbubble-therapeutic compound and/or ultrasonic energy are delivered concurrently and continuously.

5. The method of claim 1, wherein the ultrasonic energy has a peak rarefaction acoustic pressure less or equal to approximately 5.0 MPa.

6. A method of treating a vascular occlusion located at a treatment site within a patient's vasculature, the method comprising:
    passing an ultrasound assembly through the patient's vasculature to the treatment site, wherein the ultrasound assembly comprises at least one distal fluid delivery port and at least one ultrasound radiating member;
    delivering a microbubble-therapeutic compound having an initial microbubble concentration to the proximal end of the at least one distal fluid delivery port to the vascular occlusion, wherein the initial microbubble concentration is diluted to between 500,000-1,000,000 microbubble/mL, and the microbubble-therapeutic compound has a final concentration at the point of delivery to the vascular occlusion that is further reduced to 0.01% of the initial microbubble concentration; and
    delivering ultrasonic energy from the ultrasound assembly to the vascular occlusion concurrent to delivering the microbubble-therapeutic compound.

7. The method of claim 6, wherein the microbubble-therapeutic compound comprises biological or synthetic-shelled microbubbles.

8. The method of claim 7, wherein the biological or synthetic-shelled microbubbles are less than or equal to approximately 10 micrometers in diameter.

9. The method of claim 6, wherein the microbubble-therapeutic compound and/or ultrasonic energy are delivered continuously and concurrently.

10. The method of claim 6, wherein the ultrasonic energy has a peak rarefaction acoustic pressure less or equal to approximately 5.0 MPa.

* * * * *